United States Patent

Agbaje et al.

[11] Patent Number: 6,165,939
[45] Date of Patent: Dec. 26, 2000

[54] CONCENTRATE HERBICIDAL COMPOSITION

[75] Inventors: Henry E. Agbaje, St. Louis; Ronald J. Brinker, Ellisville; Deborah J. Carter, Wildwood, all of Mo.

[73] Assignee: Monsanto Company, St. Louis, Mo.

[21] Appl. No.: 09/264,591

[22] Filed: Mar. 8, 1999

Related U.S. Application Data

[60] Provisional application No. 60/077,424, Mar. 9, 1998.

[51] Int. Cl.[7] .......................... A01N 25/02; A01N 25/22; A01N 43/66; A01N 37/18; A01N 57/02
[52] U.S. Cl. .......................... 504/105; 504/107; 504/128
[58] Field of Search .................................. 504/105, 107, 504/128

[56] References Cited

U.S. PATENT DOCUMENTS

| | | | |
|---|---|---|---|
| 4,075,002 | 2/1978 | Drewe et al. | 71/92 |
| 4,826,863 | 5/1989 | Szego et al. | 514/395 |
| 4,931,086 | 6/1990 | Moucharafieh | 71/93 |
| 4,936,901 | 6/1990 | Surgant et al. | 71/92 |
| 5,074,905 | 12/1991 | Frisch et al. | 71/120 |
| 5,152,823 | 10/1992 | Albrecht et al. | 71/79 |
| 5,206,021 | 4/1993 | Dookhith et al. | 424/405 |
| 5,362,707 | 11/1994 | Fiard et al. | 504/234 |
| 5,652,197 | 7/1997 | Claude et al. | 504/206 |
| 5,750,468 | 5/1998 | Wright et al. | 504/206 |
| 5,834,006 | 11/1998 | Smith et al. | 424/409 |

FOREIGN PATENT DOCUMENTS

| | | | |
|---|---|---|---|
| 1076077 | 9/1993 | China | A01N 37/18 |
| 0 268 574 | 5/1988 | European Pat. Off. | A01N 57/20 |
| 0 343 142 | 11/1989 | European Pat. Off. | A01N 25/04 |
| 0 503 989 | 9/1992 | European Pat. Off. | A01N 25/04 |
| 6-092801 | 4/1994 | Japan | A01N 25/04 |

OTHER PUBLICATIONS

Memula et al., Pesticide Formulations and Application Systems 15, 132–144 (1996).
Tadros, Proceedings 8th International Congress of Pesticide Chemistry, 76–86 (1995).
Seaman, Pesticide Science 29, 437–449 (1990).
Mulqueen et al., Pesticide Science 29, 451–465 (1990).
Tadros, Advances in Colloid and Interface Science 32, 205–234 (1990).
Mulqueen et al., Pesticide Science and Biotechnology, 273–278 (1987).
Chemical Abstracts 120:238296 (1994): Chinese Patent Application No. 1076077.
Derwent Abstract 94–147814 (1994): Japanese Patent Application No. 06–092801.

*Primary Examiner*—S. Mark Clardy
*Attorney, Agent, or Firm*—James C. Forbes

[57] ABSTRACT

There is provided a concentrate herbicidal composition comprising a first herbicide selected from glyphosate and glufosinate, a second herbicide that is a chloroacetamide, e.g., acetochlor or metolachlor, and a third herbicide that is a triazine, e.g., atrazine, wherein the composition is a suspoemulsion having an aqueous phase, an oil phase, and particles dispersed in the aqueous and/or oil phases, and is stabilized by a stabilizing amount of one or more emulsifiers. Also provided is a method of use of a composition of the invention for killing or controlling weeds in a field.

26 Claims, No Drawings

CONCENTRATE HERBICIDAL COMPOSITION

This application claims the benefit of provisional application Ser. No. 60/077,424 filed Mar. 9, 1998.

FIELD OF THE INVENTION

The present invention relates to liquid concentrate herbicidal compositions that exhibit acceptable chemical and physical stability in normal storage conditions and that, upon dilution in a suitable volume of water, are suitable for application to plants and soil as broad-spectrum herbicides. More particularly, the present invention relates to such liquid concentrate herbicidal compositions having at least three herbicidally active ingredients.

BACKGROUND OF THE INVENTION

When growing crops in a field, it is important to kill or control the growth of undesirable plants (weeds) in the field. If not controlled, the weeds compete with crop plants for essential resources such as soil nutrients, water and sunlight. By removing a fraction of these resources or otherwise reducing the availability of these resources to crop plants, the weeds therefore restrict crop growth, resulting in loss of crop yield. Uncontrolled weeds can also have other deleterious effects; for example, weeds present during important operations in the growing of a crop, such as harvest of the crop, can impede these operations, thereby increasing the cost of production.

Timely and judicious use of herbicides can provide the required degree of weed control to avoid crop losses and minimize production costs. Herbicides such as glyphosate or glufosinate that are effective when deposited on foliage of weeds are applied, typically by spraying, post-emergence of the weeds. These herbicides have broad spectrum, that is, they are effective at commercial use rates in controlling a wide range of weed species. They are also very damaging to crop plants if deposited on foliage of these crop plants, except where the crop plants are of a variety selected, whether through traditional breeding methods or through use of genetic transformation technology, to tolerate glyphosate or glufosinate without significant injury. However, glyphosate and glufosinate can generally be used safely in a field where crop plants, even those not tolerant of foliar applications of these herbicides, have not yet emerged as seedlings from the soil. Thus a common method of use of glyphosate or glufosinate herbicides is "pre-plant" application, i.e., before planting of a crop, or "at-planting" application, i.e., immediately before, during or after planting but before emergence of the crop, to weeds that have already emerged.

Weeds tend to emerge over an extended period of time during the early part of a crop growing season. A single pre-plant or at-planting application of glyphosate or glufosinate does nothing to control weeds that have not yet emerged at the time of application, as these herbicides typically have substantially no residual action in the soil at the rates commercially used. It has therefore been known to combine, in a single spraying operation, application of one of these foliar-acting herbicides with application of one or more soil-acting residual herbicides to control weeds that would otherwise emerge after application. Such residual herbicides preferably have sufficient duration of residual activity to control weed emergence up to the time where the crop itself is sufficiently vigorous and has developed a sufficient canopy to suppress the growth of late-emerging weeds. The combination of foliar-acting and residual herbicides has been applied as a tank mixture, i.e., by admixing two or more concentrate compositions, each containing at least one active ingredient, with a suitable volume of water in the tank of a sprayer before application.

Particularly where the crop being grown is corn (maize), tank mixtures of a foliar-acting herbicide with either or both of a residual herbicide of the chloroacetamide class and/or a residual herbicide of the triazine class are known. For example, Harness® Xtra 5.6L herbicide of Monsanto Company, which contains as active ingredients the chloroacetamide herbicide acetochlor and the triazine herbicide atrazine, is labelled by the manufacturer for use in tank mixture with Roundup® herbicide of Monsanto Company, which contains as active ingredient the foliar-acting herbicide glyphosate in the form of its isopropylammonium salt. Likewise, Roundup® Ultra herbicide of Monsanto Company, which contains as active ingredient the foliar-acting herbicide glyphosate in the form of its isopropylammonium salt, is labelled by the manufacturer for use in tank mixture with each of the following: atrazine; Bicep® and Bicep® II herbicides of Novartis, which contain as active ingredients atrazine and the chloroacetamide herbicide metolachlor; Bladex® herbicide of American Cyanamid, which contains as active ingredient the triazine herbicide cyanazine; Bullet® and Lariat® herbicides of Monsanto Company, which contain as active ingredients the chloroacetamide herbicide alachlor and atrazine; Dual® and Dual® II herbicides of Novartis, which contain as active ingredient metolachlor; Extrazine® herbicide of Du Pont, which contains as active ingredients atrazine and cyanazine; Frontier® herbicide of BASF, which contains as active ingredient the chloroacetamide herbicide dimethenamid; Guardsman® herbicide of BASF, which contains as active ingredients dimethenamid and atrazine; Harness® herbicide of Monsanto Company and Surpass® and TopNotch® herbicides of Zeneca, which contain as active ingredient acetochlor; Harness® Xtra and Harness® Xtra 5.6L herbicides of Monsanto Company and Surpass® 100 herbicide of Zeneca, which contain as active ingredients acetochlor and atrazine; Lasso®, Micro-Tech® and Partner® herbicides of Monsanto Company, which contain as active ingredient alachlor; and the triazine herbicide simazine.

In general, chloroacetamide herbicides have deficiencies in their weed spectrum, especially among broadleaf (dicotyledonous) weed species, which can be ameliorated by inclusion of a triazine herbicide in the mixture.

Although tank mixtures of a broad-spectrum foliar-acting herbicide, a chloroacetamide herbicide and a triazine herbicide give satisfactory weed control performance, a need exists for a concentrate herbicidal composition containing all three of these ingredients in suitable amounts relative to each other. Such a composition would require only to be diluted in water to be ready for application, avoiding the need for tank mixing and the problems attendant therewith. In particular, a need exists for a liquid concentrate herbicidal composition that can readily be poured and metered by volume.

Concentrate compositions containing a plurality of active ingredients are typically difficult to formulate because of differing physical properties of the various ingredients and, in some cases, physical and/or chemical incompatibility of the ingredients. Difficulties in formulation are compounded when, as in the case of most commercial herbicide products, the composition must show acceptable storage stability for a period of at least about 30 days, preferably at least about 6 months, under normal storage conditions. Achieving such storage stability is especially difficult where a first active ingredient (e.g., a salt of glyphosate) is highly water-soluble, a second active ingredient (e.g., acetochlor) is liquid at ambient temperature and of very low solubility in water, and a third active ingredient (e.g., atrazine) is solid at ambient temperature and of low solubility both in water and in suitable organic solvents, including the second, liquid, active ingredient.

U.S. Pat. No. 4,075,002 to Drewe et al. discloses herbicidal compositions comprising a solid particulate herbicide, for example a triazine such as atrazine, simazine or ametryn, dispersed in an aqueous solution of a bipyridylium salt herbicide, for example paraquat dichloride.

European Patent Application No. 0 268 574 ('574) discloses herbicidal compositions comprising an aqueous medium having dissolved therein a water-soluble salt of glyphosate and having dispersed therein two substantially water-insoluble active ingredients, namely simazine and diuron, each in solid particulate form. Also present in the disclosed compositions are a first surfactant which is a phosphate ester of an ethoxylated aralkylated phenol and a second surfactant which is an ethoxylated $C_{8-18}$ alkanoyl ester of sorbitan and/or an ethoxylated $C_{14-20}$ alcohol, together with a thickener.

European Patent Application No. 0 343 142 discloses herbicidal compositions similar to those of '574 except that the first surfactant is a propylene oxide/ethylene oxide block copolymer, the second surfactant is an ethoxylated $C_{8-18}$ alkanoyl ester of sorbitan, and a third surfactant is also present, being an ethoxylated fatty amine.

U.S. Pat. No. 5,152,823 to Albrecht et al. discloses aqueous herbicidal compositions comprising at least one water-soluble herbicide such as a salt of glyphosate or glufosinate and at least two herbicides present in disperse form, for example a triazine herbicide (e.g., atrazine, cyanazine, simazine) and a urea herbicide (e.g., diuron, chlortoluron, isoproturon, monolinuron, linuron). Surfactants present in the disclosed compositions include alkyl ether sulfates combined with ethoxylated fatty alcohols and sulfosuccinic monoesters.

U.S. Pat. No. 4,936,901 to Surgant et al. discloses solid water-dispersible granular herbicidal compositions comprising an encapsulated herbicide and at least one non-encapsulated herbicide. The encapsulated herbicide is exemplified by the chloroacetamide herbicide alachlor, and the non-encapsulated herbicide by the triazine herbicide atrazine or by a salt of glyphosate.

A form of liquid concentrate composition that has been used or advocated for herbicidal products, including those containing more than one active ingredient, is a suspoemulsion. The principles of preparing suspoemulsions have been described in the literature, for example by Mulqueen, P. J. et al.: "Suspension emulsions—a new look at tank mix technology in one pack", *Pesticide Science and Biotechnology*, 273–278 (1987) London: Blackwell; Mulqueen, P. J. et al.: "Recent developments in suspoemulsions", *Pesticide Science* 29, 451–465 (1990); Seaman, D.: "Trends in the formulation of pesticides—an overview", *Pesticide Science* 29, 437–449 (1990); Tadros, T. F.: "Disperse systems in pesticidal formulations", *Advances in Colloid and Interface Science* 32, 205–234 (1990); Tadros, T. F.: "Dispersions and dispersible systems", *Proceedings, 8th International Congress of Pesticide Chemistry*, 76–86 (1995); Winkle, J. R.: "Suspoemulsion technology and trends", *Pesticide Formulation Adjuvant Technology*, 175–185 (1996) Boca Raton: CRC; and Memula, S. et al.: "Suspoemulsions with improved stability and correlation of long term stability with the zeta potential", *Pesticide Formulations and Application Systems* 15, 132–144 (1996).

U.S. Pat. No. 5,362,707 to Fiard et al. discloses a herbicidal suspoemulsion composition comprising a solid particulate herbicide such as atrazine, and containing a sucroglyceride surfactant as an emulsifying and/or dispersing agent. No oil-soluble herbicide is disclosed to be present in the oil phase, and no water-soluble herbicide is disclosed to be present in the aqueous phase.

U.S. Pat. No. 5,206,021 to Dookhith et al. discloses stable oil-in-water emulsions containing pesticidal substances such as herbicides in both oil and aqueous phases. It is further disclosed that suspoemulsions can be prepared from such emulsions by addition of a solid pesticidal substance. The compositions disclosed contain a dispersing or stabilizing agent based on titanium dioxide.

U.S. Pat. No. 5,074,905 to Frisch et al. discloses suspoemulsion compositions containing two active ingredients such as herbicides, one in the organic or oil phase and one in the solid particulate phase. It is suggested that "in princuple, water-soluble active ingredients may also be dissolved in the aqueous phase". The disclosed compositions contain an ethylene oxide/propylene oxide block copolymer in the organic phase.

U.S. Pat. No. 4,931,086 to Moucharafieh discloses a herbicidal composition prepared by mixing an oil phase that comprises a liquid thiolcarbamate herbicide and an aqueous phase wherein is suspended a solid particulate triazine herbicide. Also present are an anionic emulsifier that is a calcium alkylbenzene sulfonate, a nonionic or modified nonionic emulsifier of defined formula, a water-soluble wetting agent that is a polyoxyethylene alkylphenol, a first dispersing agent that is a calcium lignin sulfonate, a second dispersing agent that is fumed silica, and an anti-foaming agent. No water-soluble herbicide is disclosed to be present in the aqueous phase.

U.S. Pat. No. 4,826,863 to Szego et al. discloses a suspoemulsion composition in which a water-insoluble active ingredient such as a herbicide is suspended. No herbicides are disclosed to be present in the oil phase or in solution in the aqueous phase.

European Patent Application No. 0 503 989 discloses a herbicidal composition described as a suspoemulsion having a solid particulate phase comprising for example a triazine herbicide such as atrazine, simazine or ametryn. The oil phase comprises sucroglyceride surfactants but no herbicide is disclosed to be present in the oil phase. No water-soluble herbicide is disclosed to be present in the aqueous phase.

Japanese Patent Application No. 06092801 appears from Derwent Abstracts 94-147814 to disclose an aqueous "suspension-emulsion" herbicidal composition comprising a herbicide of low water solubility that is liquid at ambient temperature and is dispersed in the aqueous phase in the form of a microemulsion, and a herbicide of low water solubility that is solid at ambient temperature and is dispersed in solid particulate form in the composition. The composition contains surfactants including calcium dodecylbenzene sulfonate, ethoxylated styrylphenyl ether and ethoxylated castor oil, and a "thixotropic agent" such as ammonium bentonite or finely particulate silica or aluminum oxide. No water-soluble herbicide appears to be disclosed as being present in the aqueous phase.

Chinese Patent Application No. 1076077 appears from Chemnical Abstracts 120:238296 to disclose an aqueous suspoemulsion comprising acetochlor and a "symtriazine" herbicide that further contains emulsifiers, dispersing agents, specific gravity adjusting agents such as isopropanol, thickeners, stabilizers, permeating agents and frost-preventing agents. No water-soluble herbicide appears to be disclosed as being present in the aqueous phase.

That preparation of a stable liquid concentrate three-phase composition containing herbicidal active ingredients in each of the three phases is not a simple matter can be demonstrated by mixing together commonly-used commercial formulations of the various ingredients in the desired proportions. For example, a three-phase composition containing 6% glyphosate, 22% acetochlor and 16% atrazine can be prepared by thoroughly homogenizing, with the appropriate amount of water, Roundup® Ultra herbicide of Monsanto Company (a formulation of glyphosate isopropylammonium salt), Harness® EC herbicide of Monsanto Company (a formulation of acetochlor) and a commercial aqueous suspension formulation of atrazine in the appropriate proportions. This composition shows serious formulation instability, as evidenced within 24 hours by flocculation of the atrazine particles and separation of an aqueous phase and oil phase. Similar problems arise if Roundup(®) Ultra herbicide is thoroughly homogenized with Harness® Xtra herbicide of Monsanto Company (a formulation of acetochlor and atrazine).

SUMMARY OF THE INVENTION

There is now provided a concentrate herbicidal composition comprising a first herbicide selected from glyphosate and glufosinate, a second herbicide that is a chloroacetamide, and a third herbicide that is a triazine, wherein the composition is a suspoemulsion having an aqueous phase, an oil phase, and particles dispersed in the aqueous and/or oil phases, and is stabilized by a stabilizing amount of one or more emulsifiers.

More particularly, there is now provided a concentrate herbicidal composition in the form of a suspoemulsion having an aqueous phase, an oil phase and a solid particulate phase, wherein at least one herbicidal active ingredient is present in each of these phases. The composition comprises (i) water;

(ii) in solution in the water, one or more salts of one or more foliar-acting herbicide(s) selected from glyphosate and glufosinate, in an acid equivalent (a.e.) concentration of about 3% to about 30% by weight of the composition as a whole;

(iii) in the oil phase, one or more chloroacetamide herbicide(s), in a concentration of about 5% to about 40% by weight of the composition as a whole;

(iv) in the solid particulate phase, one or more triazine herbicide(s), in a concentration of about 5% to about 25% by weight of the composition as a whole;

(v) a stabilizing system in an amount effective to stabilize dispersion of the oil phase in the aqueous phase and the solid particulate phase in the aqueous and/or oil phases such that the composition exhibits substantially no phase separation, sedimentation or flocculation following storage at 20–25° C. for a period of 24 hours, the stabilizing system comprising at least two surfactants having a hydrophile-lipophile balance (HLB) of about 5 to about 13, at least one of the surfactants being nonionic and the other being nonionic or anionic; and (vi) unless already included as part of the stabilizing system, one or more activating agent(s) selected from surfactants as defined below, in a total amount of about 1 to about 30 parts by weight per 10 parts by weight of the foliar-active herbicide expressed as acid equivalent;

the total amount of surfactants having HLB of about 5 to about 13 in the composition being more than 60% by weight of all surfactants in the composition.

The term "chloroacetamide" herein relates to a herbicidal compound having a structural formula that comprises a moiety

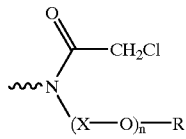

where the wavy line represents a bond to a carbon atom that is part of a ring structure, X is a linear or branched $C_{1-4}$ alkylene group, n is 0 or 1 and R is a $C_{1-4}$ linear or branched alkyl or alkenyl group. Such compounds include without restriction acetochlor, alachlor, butachlor, dimethachlor, dimethenamid, metolachlor, pretilachlor, propachlor and propisochlor. Also embraced by the term "chloroacetamide" are metazachlor and thenylchlor.

Certain chloroacetamide herbicides exhibit chirality such that certain enantiomers are herbicidally active and others substantially inactive. In such herbicides, which include metolachlor and dimethenamid, racemic mixtures are herbicidally active because they contain a herbicidally active enantiomer. Whenever reference is made herein to herbicides known to exhibit chirality, it is to be understood that such reference applies both to racemic mixtures and to herbicidally active enantiomers, unless the context demands otherwise. In particular, unless the context demands otherwise, all reference to "metolachlor" herein applies to the racemic mixture of 1S- and 1R-enantiomers and to the herbicidally active 1S-enantiomer sometimes designated "S-metolachlor".

The term "triazine" herein relates to a herbicidal compound having a structural formula that comprises a substituted 1,3,5-triazine ring and does not comprise a sulfonylurea moiety. Such compounds include without restriction ametryn, atrazine, cyanazine, desmetryn, dimethametryn, prometon, prometryn, propazine, simazine, simetryn, terbumeton, terbuthylazine, terbutryn and trietazine.

Components of the stabilizing system are selected and are included in amounts such that, as indicated above, substantially no phase separation, sedimentation or flocculation is exhibited by the suspoemulsion composition when stored at 20–25° C. for 24 hours. By "phase separation" herein is meant segegation as distinct layers in the composition of the aqueous phase and the oil phase or of components of these phases. By "sedimentation" herein is meant separation of all or part of the solid particulate phase from the liquid (aqueous and oil) phases and accumulation of the solid particulate phase at the bottom of the composition. By "flocculation" herein is meant aggregation of solid particles to form aggregates, whether or not such aggregates accumulate by sedimentation at the bottom of the composition.

The phrase "substantially no phase separation, sedimentation or flocculation" as used herein does not exclude from the invention compositions exhibiting the well-known phenomena of top-clearing or bottom-clearing. "Top-clearing" is a visible increase in transparency of the composition in a zone at the top of the composition, and can be an indication of incipient phase separation and/or sedimentation. "Bottom-clearing" is a visible increase in transparency of the composition in a zone at the bottom of the composition, and can be an indication of incipient phase separation. However, although inconvenient, neither top-clearing nor bottom-clearing is an insurmountable problem in commercial practice, as compositions which have top-cleared or bottom-cleared are readily rehomogenized by simple agitation, recirculation or inversion of the container holding such compositions. Most commercial aqueous suspension and suspoemulsion concentrate formulations of agricultural chemicals exhibit some degree of top-clearing or bottom-clearing when stored for prolonged periods.

Nonionic surfactants useful as components of the stabilizing system of compositions of the invention have HLB of about 5 to about 13 and include, without restriction, polyoxyalkylene primary and secondary $C_{8-20}$ alkylethers, alkoxylated acetylenic diols, polyoxyalkylene mono- and di($C_{8-20}$ alkyl)phenylethers, polyoxyalkylene di- and tristyrylphenylethers, polyoxyalkylene $C_{8-20}$ fatty acid esters, alkoxylated vegetable oils, block copolymers of ethylene oxide and propylene oxide and $C_{2-6}$ alkyl adducts thereof, glycerol $C_{8-0}$ fatty acid esters, sorbitan $C_{8-20}$ mono-, di- and tri($C_{8-20}$ fatty acid) esters, polyoxyalkylene sorbitan mono-, di- and tri($C_{8-20}$ fatty acid) esters, sucrose esters and $C_{8-20}$ alkyl polyglycosides.

Anionic surfactants useful as components of the stabilizing system of compositions of the invention have HLB of about 5 to about 13 and include, without restriction, $C_{8-20}$ alkyl carboxylates including fatty acids, $C_{8-20}$ alcohol sulfates, $C_{8-20}$ alcohol phosphate mono- and diesters, $C_{8-20}$ alcohol and ($C_{8-20}$ alkyl)phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, $C_{8-20}$ alkyl polyoxyethylene sulfosuccinates and sulfosuccinamates, and $C_{8-20}$ acyl glutamates, sarcosinates, isethionates and taurates. Cationic counterions accompanying anionic surfactants in compositions of the invention are preferably monovalent, especially where the foliar-acting herbicide is glyphosate, because of the tendency for divalent cations to form water-insoluble salts with glyphosate. Thus preferred counterions for anionic surfactants in compositions of the invention include hydrogen, sodium, potassium, ammonium and monovalent organic ammonium cations. The term "anionic" in the context of surfactants useful in the stabilizing system embraces all surfactants having an anionic moiety, and therefore includes surfactants commonly described as amphoteric or zwitterionic, wherein the counterion is internal to the surfactant molecule. However, anionic surfactants exclusive of amphoteric and zwitterionic surfactants are preferred.

The terms "alkoxylated" and "polyoxyalkylene" in the present context relate to surfactants comprising one or more polymerized or copolymerized chains of $C_{2-4}$ alkylene oxide units. The term "alkyl" is used in the sense in which it is conventionally used in surfactant-related art to embrace unsaturated as well as saturated hydrocarbyl chains, and includes linear and branched chains.

An "activating agent" as required herein is a surfactant that has a molecular structure comprising:
 (1) a hydrophobic moiety having one or a plurality of independently saturated or unsaturated, branched or unbranched, aliphatic, alicyclic or aromatic $C_{3-20}$ hydrocarbyl or hydrocarbylene groups joined together by 0 to about 7 ether linkages and having in total about 8 to about 20 carbon atoms; and either
 (2) where the hydrophobic moiety consists essentially of an aliphatic $C_{16-20}$ hydrocarbyl or hydrocarbylene chain, a hydrophilic moiety consisting essentially of a polyoxyethylene chain having on average about 10 to about 50 oxyethylene units per surfactant molecule; or
 (3) whether or not the hydrophobic moiety consists essentially of an aliphatic $C_{16-20}$ hydrocarbyl or hydrocarbylene chain, a hydrophilic moiety comprising:
  (a) an amino group that is cationic or that can be protonated to become cationic, having attached directly thereto 0 to 3 oxyethylene groups or polyoxyethylene chains, these oxyethylene groups and polyoxyethylene chains comprising on average 0 to about 50 oxyethylene units per surfactant molecule; and/or
  (b) a glycoside or polyglycoside group comprising on average no more than about 2 glycoside units per surfactant molecule.

In such surfactants the hydrophobic moiety is attached to the hydrophilic moiety in one of the following ways: (i) directly to an amino group if present, (ii) by an ether linkage incorporating an oxygen atom of one of the oxyethylene groups if present or of a terminal oxyethylene unit of one of the polyoxyethylene chains if present, or (iii) by an ether linkage to one of the glycoside units if present.

Also provided by the present invention is a herbicidal method comprising the steps of
 (i) diluting a concentrate suspoemulsion composition of the present invention in a suitable volume of water in a spray tank to form a spray composition, and
 (ii) applying the spray composition at a time $T_0$ by means of a sprayer fed from the spray tank to a soil surface in a field and to foliage of weeds that have emerged above the soil surface,
whereby the emerged weeds are killed or controlled and whereby weeds that would otherwise emerge later than $T_0$ are inhibited from emerging for a period of about 10 days immediately following $T_0$.

The term "weeds" as used herein includes all plants, including plants in the seedling stage whether or not they have yet emerged above the soil surface, other than plants arising from seeds deliberately sown or planted in the field for the purpose of raising a crop. Thus "weeds" include plants of crop species that grow from seeds not deliberately sown or planted, such as "volunteer" plants arising from seeds shed by plants of a previous crop grown in the same field, or seeds lost during a previous crop harvest.

DETAILED DESCRIPTION OF THE INVENTION

General features of contemplated compositions

Compositions of the present invention are suspoemulsions having a liquid aqueous phase, which is generally a continuous phase, a liquid oil phase, which is generally a discontinuous phase dispersed in the aqueous phase, and a solid particulate phase, which is a discontinuous phase dispersed in one or both of the liquid phases.

Suspoemulsion compositions contemplated in the invention differ from most previously described suspoemulsion formulations of agricultural chemicals in containing at least one active ingredient, specifically at least one herbicidal active ingredient, in each of the three phases. It will be recognized that in describing a particular component as being contained in a particular phase, the possibility is not excluded of small amounts of that component being present in one or both of the other phases.

In a contemplated composition, substantially all of the first herbicidal active ingredient, which is a salt of a foliar-acting herbicide selected from glyphosate and glufosinate, is present in solution in water in the aqueous phase. More than one salt of one of these herbicides, and salts of more than one of these herbicides, can optionally be present in the aqueous phase. However, in preferred compositions only one such foliar-acting herbicide is present, all or substantially all in the form of one salt. Preferably the salt is highly water-soluble, so that as high as possible a concentration of the foliar-acting herbicide can be accommodated in the aqueous phase and in the composition as a whole.

In a contemplated composition, substantially all of the second herbicidal active ingredient, which is a chloroacetamide herbicide, is present in the oil phase. Where the chloroacetamide herbicide is liquid at ambient temperatures, i.e., has a melting point below about 0° C., the oil phase can consist essentially or substantially of the chloroacetamide herbicide itself. In other words, no organic solvent is necessary, although one can optionally be included. Examples of chloroacetamide herbicides that are liquid at ambient temperatures and can be formulated in compositions of the invention without the need for an organic solvent, include acetochlor, butachlor, metolachlor and pretilachlor. Where an organic solvent is desired or required, any suitable organic solvent known in the agricultural chemical formulating art in which the chloroacetamide herbicide is adequately soluble can be used. Preferably the organic solvent is one in which the chloroacetamide herbicide is highly soluble, so that as high as possible a concentration of the chloroacetamide herbicide can be accommodated in the oil phase and in the composition as a whole. More than one chloroacetamide herbicide can optionally be present in the oil phase. However, in preferred compositions only one such chloroacetamide herbicide is present.

In a contemplated composition, substantially all of the third herbicidal active ingredient, which is a triazine herbicide, is present in the solid particulate phase. More than one triazine herbicide can optionally be present in the solid particulate phase. However, in preferred compositions only one such triazine herbicide is present.

Optionally one or more additional herbicidal active ingredients can be included in a composition of the invention. Such additional herbicidal ingredients can exist in one or more of the three phases of the suspoemulsion. Water-soluble herbicides will typically be present predominantly in the aqueous phase, while herbicides of low water solubility will typically be present in the oil phase or solid particulate phase.

Additional water-soluble herbicidal active ingredients that can optionally be included in a contemplated composition are exemplified without restriction by water-soluble forms or derivatives, such as water-soluble salts, of acifluorfen, asulam, benazolin, bentazon, bialaphos, bispyribac, bromacil, bromoxynil, chloramben, clopyralid, 2,4-D, 2,4-DB, dalapon, dicamba, dichlorprop, diclofop, difenzoquat, diquat, endothall, fenac, fenoxaprop, flamprop, fluazifop, fluoroglycofen, fluroxypyr, fomesafen, fosamine, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, TCA and triclopyr.

Additional water-insoluble herbicides that can optionally be included in a contemplated composition are exemplified without restriction by aclonifen, amidosulfuron, anilofos, azafenidin, azimsulfuron, benfluralin, benfuresate, bensulfuron-methyl, bensulide, benzofenap, bifenox, bromobutide, bromofenoxim, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cycloate, cyclosulfamuron, cycloxydim, cyhalofop-butyl, daimuron, desmedipham, dichlobenil, diclofop-methyl, diflufenican, dimefuron, dimepiperate, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, methabenzthiazuron, methyldymron, metobenzuron, metobromuron, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, primisulfuron, prodiamine, propanil, propaquizafop, propham, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, sulcotrione, sulfentrazone, sulfometuron, sulfosulfuron, tebutam, tebuthiuron, terbacil, thiazopyr, thifensulfuron, thiobencarb, tiocarbazil, tralkoxydim, triallate, triasulfuron, tribenuron, trifluralin, triflusulfuron and vernolate.

The aqueous phase and the foliar-active herbicide

Where the aqueous phase contains a salt of glufosinate, a preferred salt is the ammonium salt of glufosinate.

However, it is presently preferred that the foliar-active herbicide in the aqueous phase be a water-soluble salt of glyphosate, otherwise known as N-phosphonomethylglycine. Although glyphosate in its acid form has three acid sites, and can therefore form tribasic salts, it is preferred that the pH of the aqueous phase of a contemplated composition is not greater than about 8, at which pH value the fraction of glyphosate existing as a tribasic salt is negligibly small. Only the two acid sites that are significantly deprotonated at pH 8 are therefore considered herein. One of these is on the phosphonate moiety, and the other is on the carboxylate moiety, of the glyphosate molecule. At pH values around 7–8, divalent glyphosate anions predominate, thus the glyphosate can be considered to be present predominantly in the form of a dibasic salt. At pH values around 4, monovalent glyphosate anions predominate, thus the glyphosate can be considered to be present predominantly in the form of a monobasic salt.

It is preferred that the glyphosate be present in the form of a monobasic or dibasic salt or mixture thereof having a cationic counterion of molecular weight lower than about 100, or a mixture of such salts. In particularly preferred salts the cationic counterion is monovalent and is selected from alkali metal cations, ammonium cations, and organic ammonium and sulfonium cations having in total 1–6 carbon atoms. Illustrative cationic counterions for glyphosate suitable for use in compositions of the invention are sodium, potassium, ammonium, dimethylammonium, isopropylammonium, monoethanolammonium and trimethylsulfonium cations.

Where the foliar-active herbicide is glyphosate, the concentration of glyphosate in the composition as a whole is about 3% to about 30% a.e. by weight. Typically, in order to accommodate preferred amounts of the other active ingredients, glyphosate concentration is not greater than about 20% a.e. by weight, for example about 5% to about 15% a.e. by weight. In one preferred embodiment, the glyphosate concentration is at least 11 % a.e. by weight. Another exemplary concentration range for glyphosate is 3.6% to 10.8% a.e. by weight. Weight/volume concentrations of glyphosate depend on the specific gravity of the composition, but in preferred compositions range illustratively from about 60 to about 180 g a.e./l.

As indicated above, the aqueous phase can contain one or more additional water-soluble herbicides. Other ingredients that can optionally be added to the aqueous phase include inorganic salts. For example, an inorganic ammonium salt such as ammonium sulfate that is known to enhance herbicidal efficacy of glyphosate on certain weed species, or to reduce antagonism of glyphosate herbicidal efficacy by the chloroacetamide and/or triazine herbicides also present in the composition, can usefully be included. Illustrative inorganic salts that can be present are ammonium carbonate, ammonium bicarbonate, ammonium chloride, ammonium fluoride, ammonium nitrate, ammonium biphosphate, ammonium dihydrogen phosphate, ammonium sulfate, ammonium bisulfate, ammonium bisulfite, ammonium thiocyanate, potassium carbonate, potassium bicarbonate, potassium chloride, potassium nitrate, potassium phosphate, potassium biphosphate, potassium dihydrogen phosphate, potassium sulfate, potassium bisulfate, potassium sulfite, potassium bisulfite, sodium carbonate, sodium bicarbonate, sodium chloride, sodium nitrate, sodium phosphate, sodium biphosphate, sodium dihydrogen phosphate, sodium sulfate, sodium bisulfate, sodium sulfite and sodium bisulfite.

Another type of ingredient that can optionally be added as a component of the aqueous phase is an organic or inorganic acid or base to adjust pH of the composition. Preferred bases are sodium hydroxide, potassium hydroxide, ammonium hydroxide and organic amines such as isopropylamine.

The oil phase and the chloroacetamide herbicide

The oil phase comprises (a) a chloroacetamide herbicide, (b) an organic solvent for the chloroacetamide herbicide, this organic solvent being optional where the chloroacetamide herbicide is liquid at ambient temperature as explained above, and optionally (c) other oil-soluble ingredients.

Preferred chloroacetamide herbicides for inclusion in compositions of the invention are those that can be used for selective pre-emergence residual weed control in corn (maize, Zea mays). Of these, acetochlor (2-chloro-N-(ethoxymethyl)-N-(2-ethyl-6-methylphenyl)acetamide) and metolachlor (2-chloro-N-(2-ethyl-6-methylphenyl)-N-(2-methoxy-1-methylethyl)acetamide), both of which are liquid at ambient temperature, having melting points lower than 0° C., are particularly preferred. When preparing compositions of the invention with acetochlor or metolachlor it is preferred that no substantial amount of an organic solvent, for example no more than about 1% by weight of the composition as a whole, be present.

Where it is desired or necessary to include an organic solvent, illustrative examples of organic solvents which can be suitable in particular cases are water- immiscible aliphatic and aromatic hydrocarbons and hydrocarbyl alcohols, aldehydes and ketones, mono-, di- and trihydrocarbyl phosphates, silicone and siloxane oils, fatty acids and alkylesters and alkylamides thereof, and natural vegetable oils whether fractionated or not. Solvents of low volatility are preferred, especially those having flash point of at least about 100° C.

Where the chloroacetamide herbicide is acetochlor or metolachlor, the concentration of the chloroacetamide herbicide in the composition as a whole is about 5% to about 40% by weight. An exemplary concentration range for the chloroacetamide herbicide is 8.65% to 26% by weight. A preferred range is about 15% to about 30% by weight. Weight/volume concentrations of the chloroacetamide herbicide depend on the specific gravity of the composition, but in preferred compositions range illustratively from about 180 to about 360 g/l.

As indicated above, the oil phase optionally contains one or more additional water-insoluble herbicides. Another optional ingredient that, if included, is generally present predominantly in the oil phase, is a safener for the chloroacetamide herbicide. A safener is a compound that reduces injury by the chloroacetamide herbicide to crop plants, particularly crop plants that have not emerged above the soil surface at the time of application. Safeners are extensively used in herbicidal products containing acetochlor or metolachlor and are effective in reducing pre-emergence injury to corn by the acetochlor or metolachlor. Illustrative examples of safeners that can optionally be included in a composition of the invention are benoxacor, fenclorim, flurazole, fluxofenim, furilazole and oxabetrinil. Presently preferred safeners are benoxacor ((±)-4-(dichloroacetyl)-3,4-dihydro-3-methyl-2H-1,4-benzoxazine) and furilazole ((±)-3-(dichloroacetyl)-5-(2-furanyl)-2,2-dimethyloxazolidine). Benoxacor is especially preferred where the composition contains metolachlor, and furilazole is especially preferred where the composition contains acetochlor.

The safener, if present, should be included in an amount effective to reduce injury to crop plants caused by the chloroacetamide herbicide. Typically such an amount is provided where the chloroacetamide herbicide and the safener are present in a ratio by weight of about 5:1 to about 100:1, for example about 20:1 to about 40:1.

Where the chloroacetamide herbicide is acetochlor and the safener is furilazole, the concentration of furilazole in the composition as a whole is zero to about 1.5% by weight, for example zero to about 1% by weight. An exemplary concentration range for a safener, if present, is 0.26% to 0.78% by weight. Weight/volume concentrations of furilazole depend on the specific gravity of the composition, but in preferred compositions range illustratively from zero to about 12 g/l.

The solid particulate phase and the triazine herbicide

The solid particulate phase comprises the triazine herbicide. Optionally, other solid particulate materials can be present in a composition of the invention, including one or more additional solid particulate herbicidal active ingredients, or colloidal particulate inorganic materials such as silica, titanium dioxide or clays which can form part of the stabilizing system as described below.

Preferred triazine herbicides are those that can be used selectively for pre-emergence residual weed control in corn, for example ametryn, atrazine, cyanazine, simazine and terbuthylazine. An especially preferred triazine herbicide is atrazine (6-chloro-N-ethyl-N'-(1-methylethyl)-1,3,5-triazine-2,4-diamine).

The concentration of the triazine herbicide in the composition as a whole is about 5% to about 25% by weight. An exemplary concentration range for a triazine herbicide is 6.2% to 18.7% by weight. A preferred range is about 8% to about 20% by weight. Weight/volume concentrations of the triazine herbicide depend on the specific gravity of the composition, but in preferred compositions range illustratively from about 90 to about 180 g/l.

Median particle size of a triazine herbicide to be incorporated as the solid particulate phase of a composition of the invention is not narrowly critical. However, if particle size is too large, it can be difficult to find a stabilizing system that can keep the particles in suspension. If particle size is too small and some sedimentation occurs, the particles can hard-pack at the bottom of the container, whereafter the particles can be very difficult to resuspend. In general, a median particle size of about 3 to about 30 μm is suitable. It is preferred that <10% of the particles be larger than about 50 μm and that >90% be larger than about 0.5 μm.

The stabilizing system

Use of the term "stabilizing system" herein should not be taken to imply that such system, or components thereof, functions only in stabilizing dispersion of the oil and solid particulate phases in the aqueous phase of the concentrate composition. Components of the stabilizing system can perform additional useful functions, for example in assisting rapid and uniform dispersion of the oil and particulate phases upon dilution in water to form a spray composition. As explained more fully below, certain components of the stabilizing system can also perform as activating agents for the foliar-active herbicide.

A contemplated composition comprises a stabilizing system in an amount effective to stabilize dispersion of the oil phase and the solid particulate phase in the aqueous phase such that the composition exhibits substantially no phase separation, sedimentation or flocculation following storage at 20–25° C. for a period of 24 hours. In preferred compositions, the stabilizing system is adequate to result in substantially no phase separation, sedimentation or flocculation following storage at any temperature or sequence of temperatures in a range from about 0° C. to about 40° C., more preferably at any temperature or sequence of temperatures in a range from about 10° C. to about 50° C., for a period of at least 7 days, more preferably at least 30 days and most preferably at least 6 months.

A useful method of evaluating physical stability of a concentrate composition is to examine it for phase separation, sedimentation or flocculation following storage of the composition in a suitable container at a selected elevated temperature, e.g., 40–50° C., for a defined period, e.g., 1–100 days. The effects of such storage tend to mimic the effects of a much longer period of storage at ambient temperatures. We have found, for example, that particularly accurate prediction of long-term stability under a normal range of storage conditions can be obtained by storage at 40° C. for 12 weeks or at 50° C. for 8 weeks.

Top-clearing or bottom-clearing, even if indications of incipient instability, are generally not in themselves unacceptable. However, in especially preferred compositions of the invention, even top-clearing and bottom-clearing are exhibited only to a very minor degree if at all.

The stabilizing system preferably comprises at least one nonionic surfactant having HLB of about 5 to about 13 and at least one anionic surfactant having HLB of about 5 to about 13. Nonionic and anionic surfactants having HLB of about 8 to about 13 are preferred. The stabilizing system can optionally further comprise additional ingredients, including surfactants not meeting the criteria given immediately above and non-surfactant materials such as thickeners.

The expressions "about 5 to about 13" and "about 8 to about 13" relating to HLB herein are to be taken to encompass surfactants having HLB marginally above 13.0, for example a $C_{9-11}$ alkyl polyglucoside having an average of about 1.6 glucose units per surfactant molecule and having HLB of 13.1. However, the term "about 5 to about 13" is to be understood as excluding surfactants having HLB of 14 or higher, such as polyoxyethylene (15) tallowamine (HLB=14).

Preferred nonionic surfactants useful as components of the stabilizing system include block copolymers of ethylene oxide and propylene oxide and $C_{2-6}$ alkyl adducts thereof, polyoxyethylene sorbitan mono-, di- and tri($C_{12-20}$ alkyl) esters, and $C_{8-20}$ alkyl polyglucosides.

Preferred anionic surfactants useful as components of the stabilizing system include ($C_{8-12}$ alkyl)phenyl polyoxyethylene ether sulfates, and ($C_{8-12}$ alkyl)phenyl polyoxyethylene phosphate mono- and diesters, accompanied in each case by monovalent counterions. In one embodiment the monovalent counterion for a ($C_{8-12}$ alkyl)phenyl polyoxyethylene ether sulfate or a ($C_{8-12}$ alkyl)phenyl polyoxyethylene phosphate is a protonated polyoxyethylene $C_{12-20}$ alkylamine surfactant. In this embodiment the polyoxyethylene $C_{12-20}$ alkylamine surfactant preferably has HLB of about 5 to about 13, more preferably about 8 to about 13.

A particularly preferred composition of the invention has a stabilizing system that comprises a blend of (i) a $C_{2-6}$ alkyl adduct of a block copolymer of ethylene oxide and propylene oxide, (ii) a polyoxyethylene sorbitan mono-, di- or tri($C_{12-20}$ alkyl)ester and (iii) a polyoxyethylene $C_{12-20}$ alkylamine salt of a ($C_{8-12}$ alkyl)phenol polyoxyethylene ether sulfate. Another particularly preferred composition of the invention has a stabilizing system that comprises a blend of (i) and (ii) as given immediately above, together with (iii) a ($C_{8-12}$ alkyl)phenol polyoxyethylene phosphate ester, optionally accompanied by a polyoxyethylene $C_{12-20}$ alkylamine.

Illustrative examples of specific surfactants useful in the stabilizing system are a butyl adduct of a block copolymer of ethylene oxide and propylene oxide having HLB of 12, polyoxyethylene (20) sorbitan trioleate (HLB=11), the polyoxyethylene (5) tallowamine salt of a nonylphenol polyoxyethylene ether sulfate (HLB =8), nonylphenol polyoxyethylene (3–9) phosphate (HLB=8–13), e.g., nonylphenol polyoxyethylene (6) phosphate, and a blend of such nonylphenol polyoxyethylene (3–9) phosphate with polyoxyethylene (5) tallowamine (HLB =9).

Surfactants included as activating agents for the foliar-active herbicide, as described below, can play a secondary role as components of the stabilizing system. As one example, a $C_{9-11}$ alkyl polyglucoside having an average of about 1.6 glucose units per surfactant molecule and having HLB of about 13 is useful both as an activating agent and as a nonionic component of the stabilizing system. As a further example, polyoxyethylene (5) tallowamine is a useful activating agent and, as indicated above, can also serve as a counterion for an anionic component of the stabilizing system.

The amount of each component of the stabilizing system depends on the particular active ingredients selected for the composition and the absolute and relative amounts of these desired. Suitable amounts of stabilizing system components selected from the classes or specific examples provided herein can be determined by routine experimentation, the test being that substantially no phase separation, sedimentation or flocculation is exhibited by the composition following storage at 20–25° C. for a period of 24 hours, or, for preferred embodiments, following a longer period of storage over a broader range of temperatures as indicated above. Typically the total concentration of all nonionic surfactants having HLB of about 5 to about 13 in the composition as a whole is about 1% to about 10% by weight, for example about 1.5% to about 5% by weight. Typically the total concentration of all anionic surfactants having HLB of about 5 to about 13 in the composition as a whole is about 1% to about 10% by weight, for example about 2% to about 6% by weight, excluding the weight of counterions.

It is preferred that the total concentration of surfactants of all classes having HLB of about 5 to about 13 in the composition as a whole is not greater than about 7% by weight.

The stabilizing system, in one particularly preferred embodiment, further comprises an emulsion stabilizer that is an anionic surfactant of HLB greater than about 15. A suitable example of such an emulsion stabilizer is sodium lauryl sulfate or ammonium lauryl sulfate, either of which can illustratively be present in a concentration in the composition as a whole of zero to about 5% by weight, for example zero to about 1% by weight, excluding water or other diluent in which the emulsion stabilizer is supplied.

In a composition of a preferred embodiment of the invention, as indicated above, more than 60% by weight of all surfactants of all classes present in the composition is accounted for by surfactants having HLB of about 5 to about 13. In a particularly preferred embodiment, at least about 70% by weight of all surfactants of all classes present in the composition as a whole is accounted for by surfactants having HLB of about 5 to about 13. We have found that such preponderance of surfactants of moderately low HLB and a correspondingly low amount of surfactants of higher HLB (about 14 and higher) is associated with particularly favorable storage stability properties. We have also found that, surprisingly, post-emergence herbicidal efficacy attributable to the glyphosate or glufosinate salt is not unacceptably sacrificed or compromised by the relatively low amount of high-HLB surfactants in the composition.

In computing relative amounts of surfactants of different HLB ranges present in a composition, the weight of water or other diluent supplied with a surfactant, if known, should be excluded. For example, Stepanol™ WAC of Stepan Company contains 29% sodium lauryl sulfate. In a composition containing 1% StepanolTM WAC, the concentration of sodium lauryl sulfate should be computed as 0.29%.

In preferred embodiment of the present invention, the suspoemulsion comprised one or more emulsifiers elected from ethoxylated amines, alkyl ether sulfates, phosphates esters, sorbitan derivatives, alkyphenols and block copolymers of propylene oxide and ethylene oxide.

Optionally, the stabilizing system can further comprise one or more thickeners, including any viscosity increasing or thixotropic agent known in the art. Certain surfactants, including representatives of nonionic and anionic surfactant classes identified above, can act as thickeners. Inert solid particulates useful as thickeners include microparticulate and nanoparticulate silica, titanium dioxide, aluminum oxide, attapulgites, montmorillonites, bentonites and diatomites. Gums useful as thickeners include xanthan, gellan and guar gums. Polymers useful as thickeners include polyethylene and polypropylene glycols, polyacrylates, polyacrylamides, polyethyleneimines, polyvinyl alcohol, polyvinyl acetate, methyl-, hydroxyethyl- and hydroxypropylcelluloses and derivatives thereof, starches and derivatives thereof, etc.

Preferred thickeners where included are colloidal microparticulate silica and clays, such as colloidal attapulgite. Clays that have a tendency to bind the foliar-active herbicide or otherwise render it insoluble in water or unavailable for foliar uptake should be used sparingly in the composition, to avoid loss of foliar herbicidal activity. Colloidal silica and/or attapulgite clay can illustratively be present in a total concentration in the composition as a whole of zero to about 5% by weight, in preferred compositions zero to about 1% by weight.

The activating agent(s)

Two subclasses of surfactant are particularly useful as activating agents in compositions of the invention, particularly where the foliar-active herbicide is a salt of glyphosate.

The first subclass has, at a pH level of about 4, the formula

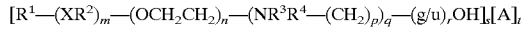

where $R^1$ is hydrogen or $C_{1-18}$ hydrocarbyl, each X is independently an ether, thioether, ester, thioester or amide linkage, each $R^2$ is independently $C_{3-6}$ hydrocarbylidene, m is an average number of 0 to about 8, the total number of carbon atoms in $R^1$—$(XR^2)_m$ is about 8 to about 24, n is an average number of 0 to about 5, $R^3$ and $R^4$ are independently hydrogen or $C_{1-4}$ alkyl, p is 2 to 4, q is 0 or 1, glu is a unit of formula

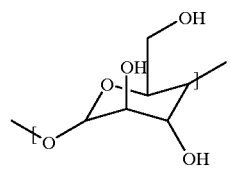

(referred to herein as a glucoside unit), r is an average number from 1 to about 2, A is an anionic entity, and s is an integer from 1 to 3 and t is 0 or 1 such that electrical neutrality is maintained.

The second subclass has, at a pH level of about 4, the formula

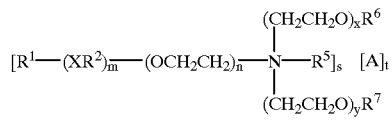

where $R^1$ is hydrogen or $C_{1-18}$ hydrocarbyl, each X is independently an ether, thioether, ester, thioester or amide linkage, each $R^2$ is independently $C_{3-6}$ hydrocarbylidene, m is an average number of 0 to about 9, the total number of carbon atoms in $R^1$—$(XR^2)_m$ is about 8 to about 24, n is an average number of 0 to about 5, $R^5$ is hydrogen, $C_{1-4}$ alkyl, benzyl, an anionic oxide group or an anionic group $(CH_2)_u$ C(O)O where u is 1 to 3, $R^6$ and $R^7$ are independently hydrogen, $C_{1-4}$ alkyl or $C_{2-4}$ acyl, x and y are average numbers such that x+y is 0 to about 30, A is an anionic entity and s is an integer from 1 to 3 and t is 0 or 1 such that electrical neutrality is maintained.

It will be appreciated that surfactants of the two subclasses described above include non-restrictively those that can be described as alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene N-methyl alkylammonium salts, polyoxyethylene N-methyl alkyletherammonium salts, alkyldimethylamine oxides, polyoxyethylene alkylamine oxides, polyoxyethylene alkyletheramine oxides, alkylbetaines, alkylamidopropylamines and the like.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Illustrative surfactant types that can be useful as activating agents in compositions of the invention include the following:

(A) Surfactants of the first subclass defined above where $R^1$ is a $C_{8-18}$ aliphatic, saturated or unsaturated, linear or branched hydrocarbyl chain, m, n and q are 0, s is 1 and t is 0. This group includes several commercial surfactants collectively known in the art or referred to herein as "alkyl polyglucosides" or "APGs". Suitable examples are sold by Henkel as Agrimul™ PG-2069 and Agrimul™ PG-2076.

(B) Surfactants of the second subclass defined above where $R^1$ is a $C_{8-18}$ aliphatic, saturated or unsaturated, linear or branched hydrocarbyl chain and m is 0. In this group $R^1$ alone forms the hydrophobic moiety of the surfactant and is attached directly to the amino function, as in alkylamines, or by an ether linkage formed by the oxygen atom of an oxyethylene group or the terminal oxygen atom of a polyoxyethylene chain, as in certain alkyletheramines. Illustrative subtypes having different hydrophilic moieties include:

(B-1) Surfactants wherein x and y are 0, $R^5$, $R^6$ and $R^7$ are independently hydrogen or $C_{1-4}$ alkyl and t is 1. This subtype includes (where $R^5$, $R_6$ and $R_7$ are each methyl and A is a chloride ion) several commercial surfactants known in the art or referred to herein as "alkyltrimethylammonium chlorides". A suitable example is cocoalkyl trimethylammonium chloride, available for example from Akzo as Arquad™ C. This subtype also includes (where $R^5$ and $R^6$ are each methyl, $R^7$ is hydrogen and A is a glyphosate ion) several commercial materials known in the art or referred to herein in their unprotonated state as "alkyldimethylamines". Suitable examples include cocoalkyldimethylamine and tallowalkyldimethylamine.

(B-2) Surfactants wherein x+y is 2 to about 30, $R^6$ and $R^7$ are hydrogen and t is 1. This subtype includes commercial surfactants known in the art or referred to herein as "polyoxyethylene alkylamines" (where n is 0 and $R^5$ is hydrogen), certain "polyoxyethylene alkyletheramines" (where n is 1–5 and $R^5$ is hydrogen), "polyoxyethylene N-methyl alkylammonium chlorides" (where n is 0 and $R^5$ is methyl), and certain "polyoxyethylene N-methyl alkyletherammonium chlorides" (where n is 1–5 and $R^5$ is methyl). Suitable examples are polyoxyethylene (2) cocoamine, polyoxyethylene (5) tallowamine, polyoxyethylene (10) cocoamine and polyoxyethylene (15) tallowamine, available for example from Akzo as Ethomeen™ C/12, Ethomeen™ T/15, Ethomeen™ C/20 and Ethomcen™ T/25 respectively, a surfactant conforming, when its amine group is non-protonated, to the formula

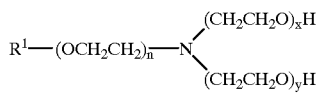

where $R^1$ is $C_{12-15}$ alkyl and x+y is 5, as disclosed in U.S. Pat. No. 5,750,468, and polyoxyethylene (2) N-methyl cocoammonium chloride, polyoxyethylene (2) N-methyl stearylammonium chloride and polyoxyethylene (15) N-methyl cocoammonium chloride, available for example from Akzo as Ethoquad™ C/12, Ethoquad™ 18/12 and Ethoquad™ C/25 respectively. In cases where $R^5$ is hydrogen, i.e., in tertiary as opposed to quaternary ammonium surfactants, the anion A is typically not supplied with the surfactant. However, in a glyphosate-containing formulation at a pH of about 4–5, it will be recognized that the anion A can be glyphosate, which is capable of forming dibasic salts.

(B-3) Surfactants wherein $R^5$ is an anionic oxide group and t is 0. This subtype includes commercial surfactants known in the art or referred to herein as "dimethyl alkylamine oxides" (where n, x and y are 0, and $R^6$ and $R^7$ are methyl), certain "dimethyl alkyletheramine oxides" (where n is 1–5, x and y are 0, and $R^6$ and $R^7$ are methyl), "polyoxyethylene alkylamine oxides" (where n is 0, x+y is 2 or greater, and $R^6$ and $R^7$ are hydrogen), and certain "polyoxyethylene alkyletheramine oxides" (where n is 1–5, x+y is 2 or greater, and and $R^6$ and $R^7$ are hydrogen). Suitable examples are dimethyl cocoamine oxide, sold by Akzo as Aromox™ DMC, and polyoxyethylene (2) cocoamine oxide, sold by Akzo as Aromox™ C/12.

(B-4) Surfactants wherein $R^5$ is an anionic group —$CH_2C(O)O$ (acetate), x and y are 0 and t is 0. This subtype includes commercial surfactants known in the art or referred to herein as "alkyl betaines" (where n is 0, $R^5$ is acetate and $R^6$ and $R^7$ are methyl) and certain "alkylether betaines" (where n is 1–5, $R^5$ is acetate and $R^6$ and $R^7$ are methyl). A suitable example is cocobetaine, sold for example by Henkel as Velvetex™ AB-45.

(C) Surfactants of the second subclass where $R^1$ is a $C_{8-18}$ aliphatic, saturated or unsaturated, linear or branched hydrocarbyl chain, m is 1, X is an ether linkage, $R^2$ is n-propylene and n is 0. In this group $R^1$ together with $OR^2$ forms the hydrophobic moiety of the surfactant which is attached directly by the $R_2$ linkage to the amino function. These surfactants form a category of alkyletheramines as disclosed in U.S. Pat. No. 5,750,468. Illustrative subtypes have the different hydrophilic moieties exemplified in (B-1) to (B-4) above. Suitable examples are a surfactant conforming, when its amine group is non-protonated, to the formula

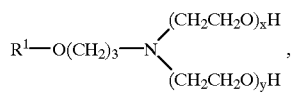

a surfactant conforming to the formula

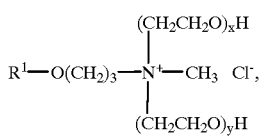

and a surfactant conforming to the formula

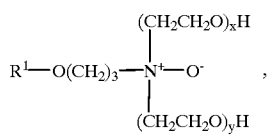

where, in each of the three formulas immediately above, $R^1$ is $C_{12-15}$ alkyl and x +y is 5, as disclosed in U.S. Pat. No. 5,750,468.

(D) Surfactants of the second subclass where R' is a $C_{8-18}$ aliphatic, saturated or unsaturated, linear or branched hydrocarbyl chain, m is 1–5, each $XR^2$ is a group —$OCH(CH_3)CH_2$— and n is 0. In this group $R^1$ together with the —$OCH(CH_3)CH_2$— groups forms the hydrophobic moiety of the surfactant which is attached directly to the amino function. These surfactants form a further category of alkyletheramines as disclosed in U.S. Pat. No. 5,750,468. Illustrative subtypes have the different hydrophilic moieties exemplified in (B-1) to (B-4) above. A suitable example is a surfactant conforming, when its amine group is non-protonated, to the formula

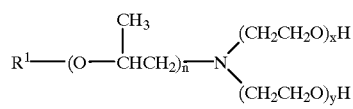

where $R^1$ is $C_{12-15}$ alkyl, m is 2 and x+y is 5 as disclosed in U.S. Pat. No. 5,750,468.

(E) Surfactants of the second subclass where $R^1$ is a $C_{8-18}$ aliphatic, saturated or unsaturated, linear or branched hydrocarbyl chain, m is 1, X is an amide linkage, $R^2$ is n-propylene and n is 0. In this group $R^1$ together with $XR^2$ forms the hydrophobic moiety of the surfactant which is attached directly by the $R^2$ linkage to the amino function. In preferred surfactants of this group, x and y are 0, $R^5$ is hydrogen or $C_{1-4}$ alkyl, $R^6$ and $R^7$ are independently $C_{1-4}$ alkyl and t is 1. A suitable example is cocoamidopropyl dimethylamine propionate, sold for example by McIntyre as Mackalene™ 117.

(F) Surfactants of the second subclass where $R^1$ is hydrogen, m is 3–8 and each $XR^2$ is a group —OCH$(CH_3)CH_2$—. In this group the polyether chain of —$OCH(CH_3)CH_2$— groups (a polyoxypropylene chain) forms the hydrophobic moiety of the surfactant which is linked directly or via one or more oxyethylene units to the amino function. In preferred surfactants of this group, x and y are 0, $R^5$, $R^6$ and $R^7$ are independently $C_{1-4}$ alkyl and t is 1. These surfactants are a subclass of the polyoxypropylene quaternary ammonium surfactants disclosed in U.S. Pat. No. 5,652,197. In a suitable example, m is 7, n is 1, $R^5$, $R^6$ and $R^7$ are each methyl, and A is chloride.

In surfactants of either subclass where t is 1, A can be any suitable anion but preferably is chloride, bromide, iodide, sulfate, ethosulfate, phosphate, acetate, propionate, succinate, lactate, citrate or tartrate, or, as indicated above, glyphosate.

In a contemplated composition, the total concentration of activating agent(s) in the composition as a whole, including surfactants contributing also to the stabilizing system, is about one-tenth to about three times the concentration of the foliar-active herbicide, expressed as acid equivalent. Typically activating agent(s) account for about 0.5% to about 20% by weight of the composition as a whole, but in preferred compositions they account for only about 0.5% to about 3% by weight. We have been surprised to find that foliar herbicidal activity of glyphosate-containing compositions of the invention having relatively low concentrations of activating agent is at least as great as that of otherwise similar compositions having much higher concentrations of activating agent. It appears that the general observation of increasing glyphosate herbicidal activity with increasing concentration of activating agent, well known in the art, is not wholly applicable in the context of the presently contemplated compositions.

Other ingredients

Optionally a contemplated composition can contain inert or excipient ingredients in addition to those mentioned above. For example, antifreeze agents or pour-point modifying agents such as glycols, e.g., diethylene glycol, propylene glycol, dipropylene glycol, or polyethylene glycol of molecular weight in the range from about 200 to about 1000, can be found useful. A typical concentration of glycols in the composition as a whole is zero to about 5% by weight. Propylene glycol at a concentration of about 0.5% to about 3% has been found particularly suitable.

As some of the surfactants present as components of the stabilizing system or as activating agents in a contemplated composition can create excessive amounts of foam, or excessively stable foam, during packaging, dispensing and/or diluting of the composition, it is often desirable to include an antifoam agent, for example an organosilicone antifoam agent. A typical concentration of antifoam agent in the composition as a whole is zero to about 0.5% by weight.

Process for making a contemplated composition

Processes described in the literature for preparing suspoemulsions are generally suitable for preparing compositions of the present invention. The invention is not limited to compositions prepared by processes described herein.

In a preferred process, an aqueous premix is first prepared by mixing together with agitation in a first vessel (a) water, (b) the water-soluble foliar-active herbicide salt, which typically is added in the form of a concentrated aqueous solution, (c) activating agents other than surfactants that also serve as nonionic components of the stabilizing system or as counterions for anionic components of the stabilizing system, (d) other optional water-soluble ingredients such as inorganic salts, glycols, and acid or base for pH adjustment, and (e) antifoam agent if included. It is particularly preferred, though not necessary, to add the foliar-active herbicide salt after all other ingredients of the aqueous premix. The ingredients of the aqueous premix are added in relative quantities calculated to provide the desired proportions of these ingredients in the finished composition.

An organic premix is also prepared by mixing together with agitation in a second vessel, preferably in the following order, (a) organic solvent if included, (b) the chloroacetamide herbicide, (c) safener if included, (d) anionic component of the stabilizing system (including counterions), and (e) nonionic component of the stabilizing system. The ingredients of the organic premix are added in relative quantities calculated to provide the desired proportions of these ingredients in the finished composition. If the activating agent or any component thereof has HLB lower than about 13, it can optionally be included in the organic premix instead of in the aqueous premix.

If a colloidal particulate thickener is to be included in the composition, a slurry of this thickener is prepared by mixing it with water in a third vessel under high shear.

The organic premix is added with agitation to the aqueous premix or vice versa in relative amounts calculated to provide the desired proportions of ingredients in the finished composition. An aqueous-organic mixture is thereby formed. Agitation of this mixture is continued, and the mixture is recirculated through a homogenizer until it forms a homogeneous emulsion.

The triazine herbicide, previously milled to suitable particle size, in an amount calculated to provide the desired proportions of ingredients in the finished composition, is then added slowly to the emulsion with continuing agitation and recirculation to form a suspoemulsion.

Finally, the emulsion stabilizer (e.g., sodium lauryl sulfate) and/or colloidal particulate slurry, if included, are added to the suspoemulsion with continuing agitation and recirculation through the homogenizer to form the finished composition of the invention. The composition can thereafter be screened to remove aggregates and other insoluble matter of excessive particle size before packaging and storage.

Method of use of a contemplated composition

In a herbicidal method of using a composition of the invention, the composition is diluted in a suitable volume of water in a spray tank to form a spray composition, which is then applied at a time $T_0$ by means of a sprayer fed from the spray tank to a soil surface in a field and to foliage of weeds that have emerged above the soil surface. The degree of dilution and the amount of spray composition applied are such as to result in (i) killing or control of the emerged weeds and (ii) inhibition, for a period of about 10 days, preferably about 30 days immediately following To, of emergence of weeds that would otherwise emerge during that period.

Although the triazine herbicide can contribute to killing or control of emerged weeds, the water-soluble foliar-active herbicide (glyphosate or glufosinate salt) is primarily responsible for this effect. Substantially all of the effect of inhibition of weed emergence, i.e., residual weed control, during the period following To is due to the chloroacetamide and triazine herbicides.

In one embodiment of the present method, the spray composition is applied to a field in which no crop is planted either shortly before or shortly after application. In this embodiment, either there is no crop of any kind present, or there is a perennial or pre-existing crop in the field such as apples, pears, cherries, plums, almonds, raspberries, citrus fruit, vines, strawberries, olives, hops, sugar cane, coffee, rubber or oil palm. Where such a crop is present, application is preferably conducted in a way that directs the spray on to soil and weed foliage without significant amounts of spray landing on foliage of the crop plants.

In another embodiment of the present method, a crop is planted within a period of time from shortly before $T_0$ until about 30 days after $T_0$. In this embodiment, it is preferred that residual control of weeds persists until canopy closure of the crop. By "canopy closure" is meant the stage of growth of the crop in the field when substantially all, for example at least about 80%, of the soil surface is overlaid by crop foliage. Weeds that emerge after canopy closure generally do not create significant problems and can often be ignored.

In yet another embodiment of the present method, a crop is planted having tolerance of the foliar-active herbicide at the rate of that herbicide to be applied. A spray composition prepared by dilution in water of a composition of the invention is applied to the foliage of both crop and weed plants and to the soil surface between and around these plants, such that the emerged weeds are killed or controlled, residual control of weeds not yet emerged is obtained for a period of at least about 10 days, preferably at least about 30 days, and the crop plants are not significantly injured.

In this embodiment, it is preferred that the crop is one that has been selected or bred, by traditional breeding methods or by methods involving genetic transformation, to be tolerant of the foliar-active herbicide. For example, where the foliar-active herbicide in the composition is glyphosate, the composition can safely be applied to foliage of a glyphosate-tolerant crop. Illustrative crops tolerant of glyphosate are those sold under the Roundup Ready® trademark of Monsanto Company and include varieties of corn (maize), cotton, soybeans and oilseed rape.

It will readily be understood that the crop must be capable of tolerating the chloroacetamide and triazine herbicides. A preferred crop exhibiting a high degree of tolerance to certain chloroacetamide and triazine herbicides is corn (maize). Where corn has not yet emerged at the time of application, certain chloroacetamide herbicides, even those such as acetochlor and metolachlor commonly used pre-emergence in corn, can in some circumstances cause injury to the corn, and in such an application it is preferred to use a composition of the invention containing a safener. Where the application is being made post-emergence to corn tolerant of the foliar-active herbicide, for example to Roundup Ready® corn, a safener is generally unnecessary.

The ingredient requiring greatest attention with regard to application rates, water volumes and conditions of application is the foliar-active herbicide, particularly where the foliar-active herbicide is a glyphosate salt. The application rate for a glyphosate-containing herbicidal composition is usually expressed as amount of glyphosate per unit area treated, e.g., grams acid equivalent per hectare (g a.e./ha). A desired herbicidal effect of a glyphosate composition is, typically and illustratively, 85% control of a plant species as measured by growth reduction or mortality after a period of time following application during which the glyphosate exerts its full herbicidal or phytotoxic effects in treated plants. Depending on plant species and growing conditions, that period of time can be as short as a week, but normally a period of at least two weeks is needed for glyphosate to exert its full effect.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate salts are used to control a very wide variety of plants worldwide.

Particularly important annual dicotyledonous plant species for control of which a composition of the invention can be used are exemplified without limitation by velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (Kochia scoparia), mallow (Malva spp.), wild buckwheat, smartweed, etc. (Polygonum spp.), purslane (Portulaca spp.), russian thistle (Salsola spp.), sida (Sida spp.), wild mustard (Sinapis arvensis) and cocklebur (Xanthium spp.).

Particularly important annual monocotyledonous plant species for control of which a composition of the invention can be used are exemplified without limitation by wild oat (*Avena fatua*), carpetgrass (Axonopus spp.), downy brome (Bromus tectorum), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial dicotyledonous plant species for control of which a composition of the invention can be used are exemplified without limitation by mugwort (Artemisia spp.), milkweed (Asclepias spp.), canada thistle (*Cirsium arvense*), field bindweed (*Convolvulus arvensis*) and kudzu (Pueraria spp.).

Particularly important perennial monocotyledonous plant species for control of which a composition of the invention can be used are exemplified without limitation by brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatumn*), reed (Phragmites spp.), johnsongrass (*Sorghum halepense*) and cattail (Typha spp.).

Other particularly important perennial plant species for control of which a composition of the invention can be used are exemplified without limitation by horsetail (Equisetum spp.), bracken (*Pteridium aquilinum*), blackberry (Rubus spp.) and gorse (*Ulex europaeus*).

If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy. However, under most conditions a herbicidal method of use of the present invention gives acceptable efficacy in the absence of such adjuvants.

Plant treatment compositions can be prepared simply by diluting a concentrate composition of the invention in water. Application of plant treatment compositions to foliage is accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

Compositions of the present invention are especially useful in no-till or minimum-tillage farming systems, but are also useful in conventional tillage systems.

A plant treatment composition is preferably dilute enough to be readily sprayed using standard agricultural spray equipment. Useful spray volumes for the present invention can range from about 25 to about 1000 liters per hectare (1/ha) or higher, but preferably about 100 to about 500 l/ha, by spray application.

Generally, preferred application rates of a composition of the invention comprising glyphosate, acetochlor and atrazine are such as to provide a glyphosate rate of about 100 to about 1500 g a.e./ha, more preferably about 250 to about 1000 g a.e./ha; an acetochlor rate of about 400 to about 6000 g/ha, more preferably about 1000 to about 4000 g/ha; and an atrazine rate of about 300 to about 4500 g/ha, more preferably about 750 to about 3000 g/ha.

EXAMPLES

The following examples are provided for illustrative purposes only and are not intended to limit the scope of the invention.

Example 1

A herbicidal suspoemulsion composition is prepared having as active ingredients glyphosate, acetochlor and atrazine, together with the safener furilazole, by the following procedure. "Surfactant M" is an activating agent containing 70% polyoxyethylene (15) tallowamine (HLB=14), in which most of the balance of the preparation is polyethylene glycol.

An aqueous premix is prepared by adding to 389 g water, in a vessel provided with means of agitation, 193 g MON 0139 of Monsanto Company (62% by weight aqueous solution of glyphosate isopropylammonium salt), 134 g Surfactant M, 15 g propylene glycol, 4 g sodium sulfite and 1.5 g Mazu™ DF 100S of BASF (organosilicone antifoam agent). To this aqueous premix is added 247 g atrazine (97% purity) powder having a median particle size of about 10 $\mu$m, 1.5 g calcium carbonate and 15 g Minugel™ 400 of Floridin (colloidal attapulgite clay). Agitation is continued for 10 minutes.

An organic premix is prepared by mixing, in a vessel provided with means of agitation, 706 g acetochlor (93% purity), 21 g furilazole, 242 g of a blend of an anionic surfactant (an alkylether sulfate) and a nonionic surfactant (an ethylene oxide/propylene oxide block copolymer) and 31 g HiSil™ 233 of PPG Industries (colloidal hydrated silica). Agitation is continued for 5 minutes.

Then 680 g of the aqueous premix and 320 g of the organic premix are combined and blended in a Waring blender at medium speed to form a homogeneous suspoemulsion. The suspoemulsion has the composition shown in Table 1 below.

TABLE 1

Composition of Example 1

| Ingredient | Weight % |
| --- | --- |
| MON 0139 (62% glyphosate isopropylammonium salt) (glyphosate a.e. 6.0) | 13.1 |
| Acetochlor (93%) | 22.6 |
| Atrazine (97%) | 16.8 |
| Furilazole | 0.7 |

TABLE 1-continued

Composition of Example 1

| Ingredient | Weight % |
| --- | --- |
| Stabilizing system: | |
| Anionic/nonionic surfactant blend | 7.7 |
| Colloidal hydrated silica | 1.0 |
| Colloidal attapulgite clay | 1.0 |
| Activating agent (Surfactant M) | 9.1 |
| Propylene glycol | 1.0 |
| Sodium sulfite | 0.3 |
| Calcium carbonate | 0.1 |
| Antifoam agent | 0.1 |
| Water (excluding water contained in above ingredients) | 26.5 |

Example 2

A herbicidal suspoemulsion having the composition shown in Table 2 below is prepared by a procedure similar to that described for Example 1. The stabilizing system comprises an anionic surfactant, Toximul™ TANS-5 of Stepan Company (an alkylphenol ether sulfate/tallowamine ethoxylate salt having HLB=8), and a blend of two nonionic surfactants, Toximul™ 8320 of Stepan Company (a butyl polyoxyalkylene block copolymer having HLB=12) and Toximul™ SEE-340 of Stepan Company (a polyoxyethylene (20) sorbitan trioleate having HLB=11). The same colloidal hydrated silica, colloidal attapulgite clay and antifoam agent are used as in Example 1.

TABLE 2

Composition of Example 2

| Ingredient | Weight % |
| --- | --- |
| MON 0139 (62% glyphosate isopropylammonium salt) (glyphosate a.e. 6.0) | 13.1 |
| Acetochlor (93%) | 22.6 |
| Atrazine (97%) | 16.3 |
| Furilazole | 0.7 |
| Stabilizing system: | |
| Anionic surfactant (Toximul ™ TANS-5) | 5.5 |
| Nonionic surfactant blend (Toximul ™ 8320/SEE-340) | 4.5 |
| Colloidal hydrated silica | 1.0 |
| Colloidal attapulgite clay | 2.0 |
| Activating agent (Surfactant M) | 9.0 |
| Propylene glycol | 1.0 |
| Sodium sulfite | 0.3 |
| Antifoam agent | 0.3 |
| Water (excluding water contained in above ingredients) | 23.7 |

The total surfactant concentration in the composition of Example 2 is 16.3% by weight, of which 10.0% by weight, i.e., 61% of the weight of all surfactants present, is accounted for by surfactants having HLB of about 5 to about 13. The composition of Example 2 exhibits acceptable storage stability in that no phase separation, sedimentation or flocculation is exhibited upon storage at 20–25° C. for at least 30 days. However, storage stability is marginal, as indicated by the fact that significant top-clearing is evident. The top-cleared zone of the composition has been found by sampling and assay to be significantly deficient in acetochlor and atrazine and enriched in glyphosate. The composition is readily rehomogenized by inversion, agitation or recirculation.

Example 3

A herbicidal suspoemulsion composition is prepared having as active ingredients glyphosate, acetochlor and atrazine, together with the safener furilazole, by the following procedure.

An aqueous premix is prepared by adding together in a first agitated tank 364.9 g water, 131.5 g MON 0139, 13.3 g of 50% aqueous sodium hydroxide, 10.0 g propylene glycol, 1.0 g sodium sulfite and 3.0 g Agnique™ DF 6889 of Henkel (organosilicone antifoam agent). Water is preferably added first and MON 0139 last, but the order of addition is not critical.

An organic premix is prepared in a second agitated tank by adding 7.3 g furilazole to 227.4 g acetochlor (93% purity) with thorough agitation to ensure complete dissolution of the furilazole in the acetochlor. Then 27.0 g of the anionic surfactant Stepfac™ 8171 of Stepan Company (a polyoxyethylene (6) nonylphenol phosphate ester) is added with continuing agitation, followed by 3.3 g of a nonionic surfactant blend of Toximul™ 8320 and Toximul™ SEE-340 and 25.8 g of the nonionic surfactant and activating agent Agrimul™ PG-2069 of Henkel (a $C_{9-11}$ alkyl polyglucoside having an average of about 1.6 glucose units per surfactant molecule, HLB=13.1) with continuing agitation to ensure complete homogenization.

The entire aqueous premix is then added to the entire organic premix or vice versa to form an aqueous-organic mixture, which is continuously agitated and recirculated through a homogenizer until a homogeneous emulsion is obtained.

Then 164.8 g atrazine (97% purity) having median particle size of about 10 μm is added to the emulsion and blended until fully incorporated to form a suspoemulsion. Next, 20.7 g Stepanol™ WAC of Stepan Company (29% aqueous sodium lauryl sulfate) is added as an emulsion stabilizer. The composition is further agitated and homogenized, and is finally screened to remove large particulates and aggregates.

The finished suspoemulsion has the composition shown in Table 3.

TABLE 3

Composition of Example 3

| Ingredient | Weight % |
| --- | --- |
| MON 0139 (62% glyphosate isopropylammonium salt) (glyphosate a.e. 6.05) | 13.15 |
| Acetochlor (93%) | 22.74 |
| Atrazine (97%) | 16.48 |
| Furilazole | 0.73 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.07 |
| Activating agent (Agrimul ™ PG-2069 included above) | |
| Propylene glycol | 1.00 |
| Sodium sulfite | 0.10 |
| Sodium hydroxide (50%) | 1.33 |
| Antifoam agent | 0.30 |
| Water (excluding water contained in above ingredients) | 36.49 |

The total surfactant concentration in the composition of Example 3 is 6.21% by weight, of which 5.61% by weight, i.e., 90% of the weight of all surfactants present, is accounted for by surfactants having HLB of about 5 to about 13. The composition of Example 3 exhibits acceptable storage stability in that no phase separation, sedimentation or flocculation is exhibited upon storage at 20–25° C. for at least 30 days. In storage stability tests at elevated temperatures, to simulate longer-term storage under ambient conditions, the composition of Example 3 exhibits no phase separation, sedimentation or flocculation following storage at 50° C. for 8 weeks or at 40° C. for 12 weeks. Substantially no top-clearing is evident even after 12 months storage under ambient conditions.

Example 4

A larger volume of a suspoemulsion having the composition shown in Table 3 above was prepared and a "shuttle" (a large refillable container widely used in agricultural chemical distribution) was filled with about 450 liters of the suspoemulsion. The shuttle and its contents were then stored in a location in St Louis, Mo. not provided with any artificial heating or cooling, so that the shuttle was exposed to exterior temperature conditions for a period of one year. No agitation was provided during storage. To demonstrate that no significant segregation of active ingredients occurred in the composition, samples of the composition were withdrawn from the top, middle and bottom of the shuttle one year after filling. The samples were assayed for acetochlor, atrazine, glyphosate and furilazole. Results are shown in

TABLE 4

| | Assay (weight %) | | | |
|---|---|---|---|---|
| Sample | Acetochlor | Atrazine | Glyphosate | Furilazole |
| top | 21.65 | 16.17 | 6.26 | 0.76 |
| middle | 21.58 | 15.65 | 6.11 | 0.75 |
| bottom | 21.61 | 16.11 | 6.20 | 0.75 |

It is surprising, especially when the complexity of the composition of this example is considered, that such a high degree of stability is exhibited. It would be expected that at least some minor degree of segregation would occur, and especially that the atrazine would show depletion at the top and enrichment at the bottom due to partial settling of the solid particulate phase of the suspoemulsion. This example provides an illustration of the outstanding storage stability properties of a composition of a preferred embodiment of the invention wherein at least about 70% by weight (in this particular instance about 90% by weight) of all surfactants present have HLB in the range from about 5 to about 13.

Example 5

A herbicidal suspoemulsion having the composition shown in Table 5 below is prepared by a procedure similar to that described for Example 3. Sodium carbonate is substituted for sodium hydroxide.

TABLE 5

Composition of Example 5

| Ingredient | Weight % |
|---|---|
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.07 |
| Activating agent (Agrimul ™ PG-2069 included above) | |
| Propylene glycol | 1.00 |

TABLE 5-continued

Composition of Example 5

| Ingredient | Weight % |
|---|---|
| Sodium sulfite | 0.10 |
| Sodium carbonate | 0.67 |
| Antifoam agent | 0.30 |
| Water (excluding water contained in above ingredients) | 37.77 |

The total surfactant concentration in the composition of Example 5 is 6.21% by weight, of which 5.61% by weight, i.e., 90% of the weight of all surfactants present, is accounted for by surfactants having HLB of about 5 to about 13. The composition of Example 3 exhibits acceptable storage stability in that no phase separation, sedimentation or flocculation is exhibited upon storage at 20–25° C. for at least 24 hours.

Example 6

A herbicidal suspoemulsion having the composition shown in Table 6 below is prepared by a procedure similar to that described for Example 3. Ammonium carbonate is substituted for sodium hydroxide and Stepanol™ AM-V of Stepan Company (28% aqueous ammonium lauryl sulfate) for Stepanol™ WAC.

TABLE 6

Composition of Example 6

| Ingredient | Weight % |
|---|---|
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ AM-V) | 2.07 |
| Activating agent (Agrimul ™ PG-2069 included above) | |
| Propylene glycol | 1.00 |
| Sodium sulfite | 0.10 |
| Ammonium carbonate | 0.67 |
| Antifoam agent | 0.30 |
| Water (excluding water contained in above ingredients) | 37.77 |

The total surfactant concentration in the composition of Example 6 is 6.19% by weight, of which 5.59% by weight, i.e., 90% of the weight of all surfactants present, is accounted for by surfactants having HLB of about 5 to about 13. The composition of Example 6 exhibits acceptable storage stability in that no phase separation, sedimentation or flocculation is exhibited upon storage at 20–25° C. for at least 24 hours.

Example 7

A herbicidal suspoemulsion having the composition shown in Table 7 below is prepared by a procedure similar to that described for Example 3.

TABLE 7

Composition of Example 7

| Ingredient | Weight % |
|---|---|
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.07 |
| Activating agent (Agrimul ™ PG-2069 included above) | |
| Propylene glycol | 1.00 |
| Sodium sulfite | 0.10 |
| Sodium hydroxide (50%) | 1.33 |
| Antifoam agent | 0.30 |
| Water (excluding water contained in above ingredients) | 37.11 |

The total surfactant concentration in the composition of Example 7 is 6.21% by weight, of which 5.61% by weight, i.e., 90% of the weight of all surfactants present, is accounted for by surfactants having HLB of about 5 to about 13. The composition of Example 7 exhibits acceptable storage stability in that no phase separation, sedimentation or flocculation is exhibited upon storage at 20–25° C. for at least 24 hours.

Example 8

A herbicidal suspoemulsion having the composition shown in Table 8 below is prepared by a procedure similar to that described for Example 3. The activating agent Surfactant M is added together with the Stepfac™ 8171.

TABLE 8

Composition of Example 8

| Ingredient | Weight % |
|---|---|
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.07 |
| Activating agent (Agrimul ™ PG-2069 included above) Surfactant M | 2.50 |
| Propylene glycol | 1.00 |
| Sodium sulfite | 0.10 |
| Sodium hydroxide (50%) | 1.00 |
| Antifoam agent | 0.30 |
| Water (excluding water contained in above ingredients) | 34.94 |

The total surfactant concentration in the composition of Example 8 is 7.96% by weight, of which 5.61% by weight, i.e., 70% of the weight of all surfactants present, is accounted for by surfactants having HLB of about 5 to about 13. The composition of Example 8 exhibits acceptable storage stability in that no phase separation, sedimentation or flocculation is exhibited upon storage at 20–25° C. for at least 24 hours.

Example 9

A herbicidal suspoemulsion having the composition shown in Table 9 below is prepared by a procedure similar to that described for Example 3.

TABLE 9

Composition of Example 9

| Ingredient | Weight % |
|---|---|
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.20 |
| Activating agent (Agrimul ™ PG-2069 included above) Surfactant M | 5.00 |
| Propylene glycol | 1.00 |
| Sodium sulfite | 0.10 |
| Sodium hydroxide (50%) | 1.00 |
| Antifoam agent | 0.30 |
| Water (excluding water contained in above ingredients) | 37.11 |

The total surfactant concentration in the composition of Example 9 is 9.75% by weight, of which 5.61% by weight, i.e., 58% of the weight of all surfactants present, is accounted for by surfactants having HLB of about 5 to about 13. The composition of Example 9 does not exhibit acceptable storage stability and is included for comparative purposes. Without being bound by theory, it is believed that the relatively high proportional amount (more than 40%) of surfactants of high HLB in this composition is at least in part responsible for the instability of the composition.

Example 10

A herbicidal suspoemulsion having the composition shown in Table 10 below is prepared by a procedure similar to that described for Example 3. The Surfactant M in this example is pre-blended with ammonium sulfate, propylene glycol and water in amounts of 20 g, 10 g, 45 g and 45 g respectively, and 5 g of this pre-blended mixture is added during preparation of the composition.

TABLE 10

Composition of Example 10

| Ingredient | Weight % |
|---|---|
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.20 |
| Activating agent (Agrimul ™ PG-2069 included above) Surfactant M | 0.83 |
| Propylene glycol | 2.88 |
| Ammonium sulfate | 0.42 |
| Sodium sulfite | 0.10 |
| Sodium hydroxide (50%) | 1.00 |
| Antifoam agent | 0.30 |
| Water (excluding water contained in above ingredients) | 34.18 |

The total surfactant concentration in the composition of Example 10 is 6.83% by weight, of which 5.61% by weight, i.e., 82% of the weight of all surfactants present, is accounted for by surfactants having HLB of about 5 to about 13. The composition of Example 10 exhibits acceptable storage stability in that no phase separation, sedimentation or flocculation is exhibited upon storage at 20–25° C. for at least 24 hours.

Example 11

A herbicidal suspoemulsion having the composition shown in Table 11 below is prepared by a procedure similar to that described for Example 3. The same pre-blended mixture of Surfactant M, ammonium sulfate, propylene glycol and water as used in Example 10 is added, but in the amount of only 2.5 g.

TABLE 11

Composition of Example 11

| Ingredient | Weight % |
| --- | --- |
| MON 0139 (62% glyphosate isopropylammonium salt) (glyphosate a.e. 5.97) | 12.98 |
| Acetochlor (95%) | 22.47 |
| Atrazine (97%) | 16.33 |
| Furilazole | 0.70 |
| Stabilizing system: | |
| Anionic surfactant (Stepfac ™ 8171) | 2.70 |
| Nonionic surfactant blend (Toximul ™ 8320/SEE-340) | 0.33 |
| Nonionic surfactant (Agrimul ™ PG-2069) | 2.58 |
| Emulsion stabilizer (Stepanol ™ WAC) | 2.20 |
| Activating agent (Agrimul ™ PG-2069 included above) Surfactant M | 0.42 |
| Propylene glycol | 1.94 |
| Ammonium sulfate | 0.21 |
| Sodium sulfite | 0.10 |
| Sodium hydroxide (50%) | 1.00 |
| Antifoam agent | 0.30 |
| Water (excluding water contained in above ingredients) | 35.74 |

The total surfactant concentration in the composition of Example 11 is 6.54% by weight, of which 5.61% by weight, i.e., 86% of the weight of all surfactants present, is accounted for by surfactants having HLB of about 5 to about 13. The composition of Example 11 exhibits acceptable storage stability in that no phase separation, sedimentation or flocculation is exhibited upon storage at 20–25° C. for at least 24 hours.

Example 12

The compositions of Examples 2, 5–8, 10 and 11 were tested for post-emergence herbicidal activity in a greenhouse test, following the standard procedure described below. The composition of Example 9 was not sufficiently stable to permit reliable testing and was not included.

Seeds of the plant species indicated are planted in 85 mm square pots in a soil mix which has previously been steam sterilized and prefertilized with a 14-14-14 NPK slow release fertilizer at a rate of 3.6 kg/m³. The pots are placed in a greenhouse with sub-irrigation. About one week after emergence, seedlings are thinned as needed, including removal of any unhealthy or abnormal plants, to create a uniform series of test pots.

The plants are maintained for the duration of the test in the greenhouse where they receive a minimum of 14 hours of light per day. If natural light is insufficient to achieve the daily requirement, artificial light with an intensity of approximately 475 microeinsteins is used to make up the difference. Exposure temperatures are not precisely controlled but average about 27° C. during the day and about 18° C. during the night. Plants are sub-irrigated throughout the test to ensure adequate soil moisture levels. Relative humidity is maintained at about 50% for the duration of the test.

Pots are assigned to different treatments in a fully randomized experimental design with 3 replications. A set of pots is left untreated as a reference against which effects of the treatments can later be evaluated. A further set of 3 replications is provided for comparative treatments with a tank-mix of Roundup® herbicide (containing glyphosate as its isopropylammonium salt), Harness® EC herbicide (containing acetochlor and furilazole) and atrazine prepared such that the tank-mix has approximately the same proportions of glyphosate a.e., acetochlor, atrazine and furilazole as the compositions of the invention. The Roundup® herbicide formulation used is that sold commercially by Monsanto Company in Canada.

Application of spray compositions to foliage is made by spraying with a track sprayer fitted with a TeeJet™ 9501E nozzle calibrated to deliver a spray volume of 187 liters per hectare (1/ha). Application is made 16 days after planting. After treatment, pots are returned to the greenhouse until ready for evaluation, 22 days after treatment (DAT).

Treatments are made using spray compositions prepared by dilution in water of the concentrate compositions of the Examples indicated. All comparisons are made at equal glyphosate acid equivalent rates. The required degree of dilution for a concentrate composition to make a spray composition is calculated from the equation $$A = RS/VC$$

where A is the volume in milliliters (ml) of the concentrate composition to be added to the spray composition being prepared, R is the desired glyphosate rate in grams of acid equivalent per hectare (g a.e./ha), S is the total volume in milliliters (ml) of spray composition being prepared, V is the application rate in liters per hectare (1/ha) of spray composition, conventionally referred to as "spray volume", and C is the concentration of glyphosate in grams of acid equivalent per liter (g a.e./l) in the concentrate composition.

For evaluation of herbicidal effectiveness, all plants in the test are examined by a single practiced technician, who records percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as the one described in this Example it is normal to apply compositions at rates which are expected to give less than 85% inhibition, as this makes it easier to discriminate among compositions having different levels of effectiveness.

Results of the test of Example 12 are given in Table 12 below. The species on which the compositions were tested are the annual broadleaf weed morningglory (Ipomoea sp., IPOSS) and the annual grass weeds giant foxtail (*Setaria faberi*, SETFA) and Japanese millet, a form of barnyardgrass (*Echinochloa crus-galli*, ECHCF). Morningglory plants were at the 3-leaf stage when treated. Giant foxtail and barnyardgrass plants were at heights of 22 cm and 17 cm respectively when treated. Each concentrate composition was tested at rates of 4.5 and 9.0 l/ha. The 20 4.5 l/ha rate provides a glyphosate rate of 314 g a.e./ha, an acetochlor rate of 1120 g/ha and an atrazine rate of 840 g/ha, and the 9.0 l/ha rate provides a glyphosate rate of 628 g a.e./ha, an acetochlor rate of 2240 g/ha and an atrazine rate of 1680 g/ha.

Then 159.9 g atrazine (99.6% purity) having median particle size of about 10 μm is added to the emulsion and blended until fully incorporated to form a suspoemulsion.

TABLE 12

Post-emergence herbicidal activity of Examples 2, 5–8, 10 and 11

| Compo-sition | Rate concentrate (l/ha) | glyphosate (g a.e./ha) | acetochlor (g/ha) | atrazine (g/ha) | % Inhibition IPOSS | SETFA | ECHCF |
|---|---|---|---|---|---|---|---|
| Tank mix |  | 314 | 1120 | 840 | 72 | 40 | 77 |
|  |  | 628 | 2240 | 1680 | 82 | 75 | 97 |
| Example 2 | 4.5 | 314 | 1120 | 840 | 73 | 47 | 37 |
|  | 9.0 | 628 | 2240 | 1680 | 100 | 72 | 62 |
| Example 5 | 4.5 | 314 | 1120 | 840 | 80 | 43 | 53 |
|  | 9.0 | 628 | 2240 | 1680 | 90 | 60 | 80 |
| Example 6 | 4.5 | 314 | 1120 | 840 | 75 | 47 | 73 |
|  | 9.0 | 628 | 2240 | 1680 | 92 | 73 | 96 |
| Example 7 | 4.5 | 314 | 1120 | 840 | 75 | 43 | 48 |
|  | 9.0 | 628 | 2240 | 1680 | 83 | 73 | 82 |
| Example 8 | 4.5 | 314 | 1120 | 840 | 83 | 47 | 65 |
|  | 9.0 | 628 | 2240 | 1680 | 90 | 65 | 83 |
| Example 10 | 4.5 | 314 | 1120 | 840 | 82 | 33 | 37 |
|  | 9.0 | 628 | 2240 | 1680 | 97 | 65 | 60 |
| Example 11 | 4.5 | 314 | 1120 | 840 | 90 | 47 | 40 |
|  | 9.0 | 628 | 2240 | 1680 | 97 | 73 | 77 |

In considering the results of this test, it should be recognized that the herbicidal activity exhibited is very largely attributable to the glyphosate component of the compositions, although it is likely that the atrazine contributed in a minor way to the observed herbicidal effect on morningglory (IPOSS). It should further be recognized that the glyphosate component of the tank-mix is accompanied by an activating agent in the form of an ingredient in Roundup® herbicide at a level designed to give a high degree of herbicidal efficacy.

Example 13

A herbicidal suspoemulsion composition is prepared having as active ingredients glyphosate, acetochlor and atrazine, with no safener, by the following procedure.

An aqueous premix is prepared by adding together in a first agitated tank a first portion of 283.5 g water, 260.1 g MON 0139, 10.0 g propylene glycol, a first portion of 1.0 g sodium sulfite and 1.0 g Agnique™ DF 6889 of Henkel (organosilicone antifoam agent). Water is preferably added first and MON 0139 last, but the order of addition is not critical.

An organic premix is prepared in a second agitated tank by adding 28.0 g of the anionic surfactant Toximul™ TANS-5 to 222.4 g acetochlor (95.5% purity), followed by 17.5 g of a nonionic surfactant blend of Toximul™ 8320 and Toximul™ SEE-340 and 10.0 g of the activating agent Toximul™ TA-5 of Stepan Company (a polyoxyethylene (5) tallowamine, HLB=9) with continuing agitation to ensure complete homogenization.

In a separate container, a clay slurry is prepared by mixing a second portion of water, a second portion of sodium sulfite and 6.6 g Minugel™ 400 for 15 minutes under high shear.

The entire aqueous premix is then added to the entire organic premix or vice versa to form an aqueous-organic mixture, which is continuously agitated and recirculated through a homogenizer for 15 minutes to obtain a homogeneous emulsion.

Next, the clay slurry is added. The composition is agitated and homogenized for a further 15 minutes and is finally screened to remove large particulates and aggregates.

The finished suspoemulsion has the composition shown in Table 13.

TABLE 13

Composition of Example 13

| Ingredient | Weight % |
|---|---|
| MON 0139 (62% glyphosate isopropylammonium salt) (glyphosate a.e. 11.96) | 26.01 |
| Acetochlor (95.5%) | 22.24 |
| Atrazine (99.6%) | 15.99 |
| Stabilizing system: |  |
| Anionic surfactant (Toximul ™ TANS-5) | 2.80 |
| Nonionic surfactant blend (Toximul ™ 8320/SEE-340) | 1.75 |
| Colloidal attapulgite clay (Minugel ™ 400) | 0.66 |
| Activating agent (Toximul ™ TA-5) | 1.00 |
| Propylene glycol | 1.00 |
| Sodium sulfite | 0.10 |
| Antifoam agent | 0.10 |
| Water (excluding water contained in above ingredients) | 28.35 |

The total surfactant concentration in the composition of Example 13 is 5.55% by weight, all of which, i.e., 100% of the weight of all surfactants present, is accounted for by surfactants having HLB of about 5 to about 13. The composition of Example 13 exhibits acceptable storage stability in that no phase separation, sedimentation or flocculation is exhibited upon storage at 20–25° C. for at least 24 hours. In storage stability tests at elevated temperatures, to simulate longer-term storage under ambient conditions, the composition of Example 3 exhibits no phase separation, sedimentation or flocculation following storage at 50° C. for 8 weeks or at 40° C. for 12 weeks.

Example 14

A herbicidal suspoemulsion having the composition shown in Table 14 below is prepared by a procedure similar to that described for Example 13.

TABLE 14

Composition of Example 14

| Ingredient | Weight % |
|---|---|
| MON 0139 (62% glyphosate isopropylammonium salt) (glyphosate a.e. 13.79) | 29.99 |
| Acetochlor (95.5%) | 27.80 |
| Atrazine (99.6%) | 14.10 |
| Stabilizing system: | |
| Anionic surfactant (Toximul ™ TANS-5) | 2.90 |
| Nonionic surfactant blend (Toximul ™ 8320/SEE-340) | 1.85 |
| Colloidal attapulgite clay (Minugel ™ 400) | 0.66 |
| Activating agent (Toximul ™ TA-5) | 1.00 |
| Propylene glycol | 1.00 |
| Sodium sulfite | 0.10 |
| Antifoam agent | 0.10 |
| Water (excluding water contained in above ingredients) | 20.50 |

The total surfactant concentration in the composition of Example 14 is 5.75% by weight, all of which, i.e., 100% of the weight of all surfactants present, is accounted for by surfactants having HLB of about 5 to about 13. The composition of Example 14 exhibits acceptable storage stability in that no phase separation, sedimentation or flocculation is exhibited upon storage at 20–25° C. for at least 24 hours. In storage stability tests at elevated temperatures, to simulate longer-term storage under ambient conditions, the composition of Example 3 exhibits no phase separation, sedimentation or flocculation following storage at 50° C. for 8 weeks or at 40° C. for 12 weeks.

Example 15

A herbicidal suspoemulsion having the composition shown in Table 15 below is prepared by a procedure similar to that described for Example 13.

TABLE 15

Composition of Example 15

| Ingredient | Weight % |
|---|---|
| MON 0139 (62% glyphosate isopropylammonium salt) (glyphosate a.e. 13.85) | 30.13 |
| Acetochlor (95.5%) | 18.62 |
| Atrazine (99.6%) | 9.59 |
| Stabilizing system: | |
| Anionic surfactant (Toximul ™ TANS-5) | 2.80 |
| Nonionic surfactant blend (Toximul ™ 8320/SEE-340) | 1.85 |
| Colloidal attapulgite clay (Minugel ™ 400) | 0.86 |
| Activating agent (Toximul ™ TA-5) | 1.00 |
| Propylene glycol | 1.00 |
| Sodium sulfite | 0.10 |
| Antifoam agent | 0.10 |
| Water (excluding water contained in above ingredients) | 33.95 |

The total surfactant concentration in the composition of Example 15 is 5.65% by weight, all of which, i.e., 100% of the weight of all surfactants present, is accounted for by surfactants having HLB of about 5 to about 13. The composition of Example 15 exhibits acceptable storage stability in that no phase separation, sedimentation or flocculation is exhibited upon storage at 20-25° C. for at least 24 hours. In storage stability tests at elevated temperatures, to simulate longer-term storage under ambient conditions, the composition of Example 3 exhibits no phase separation, sedimentation or flocculation following storage at 50° C. for 8 weeks or at 40° C. for 12 weeks.

Example 16

A greenhouse test, following the procedures of Example 12, was conducted to compare herbicidal efficacy of the compositions of Examples 13-15 with tank-mix compositions of glyphosate (in the form of Roundup® Ultra herbicide), acetochlor and atrazine at the same active ingredient ratios.

Results are given in Table 16 below. The species on which the compositions were tested are the annual broadleaf velvetleaf (*Abutilon theophrasti*, ABUTH) and the annual grass weed Japanese millet, a form of barnyardgrass (*Echinochloa crus-galli*, ECHCF). Each concentrate composition was tested at rates calculated to provide glyphosate rates of 210, 420, 630 and 840 g a.e./ha.

TABLE 16

Post-emergence herbicidal activity of Examples 13–15

| | Rate | | | | % Inhibition | |
|---|---|---|---|---|---|---|
| Composition | concentrate (l/ha) | glyphosate (g a.e./ha) | acetochlor (g/ha) | atrazine (g/ha) | ABUTH | ECHCF |
| Tank mix | | 210 | 278 | 208 | 57 | 42 |
| | | 420 | 556 | 416 | 87 | 65 |
| | | 630 | 834 | 624 | 93 | 72 |
| | | 840 | 1132 | 832 | 97 | 82 |
| Example 13 | 1.17 | 210 | 278 | 208 | 57 | 47 |
| | 2.34 | 420 | 556 | 416 | 92 | 73 |
| | 3.51 | 630 | 834 | 624 | 95 | 72 |
| | 4.68 | 840 | 1132 | 832 | 95 | 73 |
| Tank mix | | 210 | 302 | 162 | 48 | 50 |
| | | 420 | 604 | 324 | 90 | 68 |
| | | 630 | 906 | 486 | 95 | 70 |
| | | 840 | 1208 | 648 | 95 | 73 |
| Example 14 | 1.02 | 210 | 302 | 162 | 58 | 50 |
| | 2.04 | 420 | 604 | 324 | 90 | 60 |
| | 3.06 | 630 | 906 | 486 | 93 | 72 |
| | 4.08 | 840 | 1208 | 648 | 95 | 75 |
| Tank mix | | 210 | 201 | 108 | 50 | 47 |
| | | 420 | 402 | 216 | 85 | 67 |
| | | 630 | 603 | 324 | 97 | 70 |
| | | 840 | 804 | 432 | 98 | 80 |
| Example 15 | 1.02 | 210 | 201 | 108 | 57 | 58 |
| | 2.04 | 420 | 402 | 216 | 90 | 65 |
| | 3.06 | 630 | 603 | 324 | 93 | 75 |
| | 4.08 | 840 | 804 | 432 | 96 | 73 |

Each of the three compositions of the invention can be seen from the above results to give very similar herbicidal efficacy to the corresponding tank-mix treatment. It is very surprising that with such a low amount of activating agent in the compositions of the invention herbicidal efficacy should nonetheles be equivalent to a tank-mix wherein glyphosate is supplied as Roundup® Ultra herbicide, a commercial formulation contributing a much higher amount of activating agent.

Example 17

A herbicidal suspoemulsion having the composition shown in Table 17 below is prepared by a procedure similar to that described for Example 3. In this composition the foliar-active herbicide component is glufosinate as the ammonium salt thereof, which is added as a 50% glufosinate a.e. by weight aqueous solution.

TABLE 17

Composition of Example 17

| Ingredient | Weight % |
|---|---|
| Glufosinate ammonium salt (50%) | 11.12 |
| (glufosinate a.e. | 5.56) |
| Acetochlor (95%) | 33.81 |
| Atrazine (98%) | 19.66 |
| Furilazole | 1.06 |
| Stabilizing system: | |
| Anionic surfactant (Stepfac ™ 8171) | 2.25 |
| Nonionic surfactant blend (Toximul ™ 8320/SEE-340) | 0.39 |
| Nonionic surfactant (Agrimul ™ PG-2069) | 2.25 |
| Emulsion stabilizer (Stepanol ™ WAC) | 2.25 |
| Activating agent (Agrimul ™ PG-2069 included above) | |
| Propylene glycol | 1.00 |
| Sodium sulfite | 0.30 |
| Sodium hydroxide (50%) | 0.16 |
| Antifoam agent | 0.15 |
| Water (excluding water contained in above ingredients) | 25.60 |

The total surfactant concentration in the composition of Example 17 is 5.54% by weight, of which 4.89% by weight, i.e., 88% of the weight of all surfactants present, is accounted for by surfactants having HLB of about 5 to about 13. The composition of Example 17 exhibits acceptable storage stability in that no phase separation, sedimentation or flocculation is exhibited upon storage at 20–25° C. for at least 24 hours.

Example 18

A herbicidal suspoemulsion having the composition shown in Table 18 below is prepared by a procedure similar to that described for Example 13, except that an organic solvent, ExxSol™ D-130 of Exxon is included in the organic premix at a weight ratio to acetochlor of 1:10.

TABLE 18

Composition of Example 18

| Ingredient | Weight % |
|---|---|
| MON 0139 (62% glyphosate isopropylammonium salt) | 26.01 |
| (glyphosate a.e. | 11.96) |
| Acetochlor (95.5%) | 22.24 |
| Atrazine (99.6%) | 15.99 |
| Organic solvent (Exxsol ™ D-130) | 2.22 |
| Stabilizing system: | |
| Anionic surfactant (Toximul ™ TANS-5) | 2.80 |
| Nonionic surfactant blend (Toximul ™ 8320/SEE-340) | 1.75 |
| Colloidal attapulgite clay (Minugel ™ 400) | 0.56 |
| Activating agent (Toximul ™ TA-5) | 1.00 |
| Propylene glycol | 1.00 |
| Sodium sulfite | 0.10 |
| Antifoam agent | 0.10 |
| Water (excluding water contained in above ingredients) | 26.23 |

The total surfactant concentration in the composition of Example 18 is 5.55% by weight, all of which, i.e., 100% of the weight of all surfactants present, is accounted for by surfactants having HLB of about 5 to about 13. The composition of Example 18 exhibits acceptable storage stability in that no phase separation, sedimentation or flocculation is exhibited upon storage at 20–25° C. for at least 24 hours.

Example 19

A herbicidal suspoemulsion having the composition shown in Table 19 below is prepared by a procedure similar to that described for Example 13. Metolachlor (racemic mixture of 1R- and 1S-enantiomers) is included as the chloroacetamide herbicide in place of acetochlor.

TABLE 19

Composition of Example 19

| Ingredient | Weight % |
|---|---|
| MON 0139 (62% glyphosate isopropylammonium salt) | 26.01 |
| (glyphosate a.e. | 11.96) |
| Metolachlor (95%) | 22.35 |
| Atrazine (99.6%) | 15.99 |
| Stabilizing system: | |
| Anionic surfactant (Toximul ™ TANS-5) | 2.80 |
| Nonionic surfactant blend (Toximul ™ 8320/SEE-340) | 1.75 |
| Colloidal attapulgite clay (Minugel ™ 400) | 0.56 |
| Activating agent (Toximul ™ TA-5) | 1.00 |
| Propylene glycol | 1.00 |
| Sodium sulfite | 0.10 |
| Antifoam agent | 0.10 |
| Water (excluding water contained in above ingredients) | 28.34 |

The total surfactant concentration in the composition of Example 19 is 5.55% by weight, all of which, i.e., 100% of the weight of all surfactants present, is accounted for by surfactants having HLB of about 5 to about 13. The composition of Example 19 exhibits acceptable storage stability in that no phase separation, sedimentation or flocculation is exhibited upon storage at 20–25° C. for at least 24 hours.

Example 20

A herbicidal suspoemulsion having the composition shown in Table 20 below is prepared by a procedure similar to that described for Example 13. Metolachlor (racemic mixture of 1R- and 1S-enantiomers) is included as the chloroacetamide herbicide in place of acetochlor.

TABLE 20

Composition of Example 20

| Ingredient | Weight % |
|---|---|
| MON 0139 (62% glyphosate isopropylammonium salt) | 26.01 |
| (glyphosate a.e. 11.96) | |
| Metolachlor (95%) | 16.76 |
| Atrazine (99.6%) | 15.99 |
| Stabilizing system: | |
| Anionic surfactant (Toximul ™ TANS-5) | 2.80 |
| Nonionic surfactant blend (Toximul ™ 8320/SEE-340) | 1.75 |
| Colloidal attapulgite clay (Minugel ™ 400) | 0.56 |
| Activating agent (Toximul ™ TA-5) | 1.00 |
| Propylene glycol | 1.00 |
| Sodium sulfite | 0.10 |
| Antifoam agent | 0.10 |
| Water (excluding water contained in above ingredients) | 33.93 |

The total surfactant concentration in the composition of Example 20 is 5.55% by weight, all of which, i.e., 100% of the weight of all surfactants present, is accounted for by surfactants having HLB of about 5 to about 13. The composition of Example 20 exhibits acceptable storage stability in that no phase separation, sedimentation or flocculation is exhibited upon storage at 20–25° C. for at least 24 hours.

Example 21

Various handling properties of the suspoemulsion composition of Example 3 were compared with those of the suspoemulsion composition of Example 2. First, the viscosity of each composition was measured at 10° C. and a pumping test was conducted at the same temperature using an Ingersoll-Dresser pump, Model SS6, fitted to a shuttle to measure pumping rate. A standard commercial formulation, Harness® Xtra 5.6L of Monsanto Company (an acetochlor/atrazine product), was tested for comparative purposes. Results are shown in Table 21A below.

TABLE 21A

Results of viscosity and pumping test of Examples 2 and 3

| Composition | Viscosity (cPs) | Pumping rate (l/minute) |
| --- | --- | --- |
| Harness ® Xtra | 150 | 22.0 |
| Example 2 | 438 | 13.6 |
| Example 3 | 123 | 28.8 |

The composition of Example 3 has much lower viscosity than the composition of Example 2. This translates to a much faster pumping rate, which is a significant advantage in commercial use of a suspoemulsion product in agriculture.

To measure properties of spray compositions prepared from the concentrate compositions of Examples 2 and 3, each concentrate composition was diluted in tap water. In each case, 2.5 ml of the concentrate was diluted to a volume of 100 ml in a cylindrical vial. Parameters recorded were bloom—a visual assessment of the rapidity and uniformity of initial dispersion of the formulation upon dilution; dispersibility—the number of inversions of the vial necessary to completely disperse the solid particulate phase; and foam height.

Results are shown in Table 21B below.

TABLE 21B

Results of tests on diluted compositions of Examples 2 and 3

| | Example 2 | Example 3 |
| --- | --- | --- |
| Bloom | good | very good |
| Dispersibility (no. of inversions) | 5 | 3 |
| Foam height (mm) | 3 | 6 |

The preceding description of specific embodiments of the present invention is not intended to be a complete list of every possible embodiment of the invention. Persons skilled in the art will recognize that modifications can be made to the specific embodiments described here that would be within the scope of the present invention.

What is claimed is:

1. A concentrate herbicidal composition comprising a first herbicide selected from glyphosate and glufosinate, a second herbicide that is a chloroacetamide, and a third herbicide that is a triazine, wherein the composition is a suspoemulsion having an aqueous phase, an oil phase, and particles dispersed in the aqueous and/or oil phases, and is stabilized by a stabilizing amount of one or more emulsifiers.

2. A composition of claim 1 wherein said first herbicide is selected from the sodium, potassium, ammonium, dimethylammonium, isopropylammonium, monoethanolammonium and trimethylsulfonium salts of glyphosate.

3. A composition of claim 1 wherein said first herbicide is the ammonium salt of glufosinate.

4. A composition of claim 1 wherein
   (a) said first herbicide is selected from the sodium, potassium, ammonium, dimethylammonium, isopropylammonium, monoethanolammonium and trimethylsulfonium salts of glyphosate;
   (b) said chloroacetamide herbicide is acetochlor;
   (c) said triazine herbicide is atrazine; and
   (d) said emulsifiers comprise one or more emulsifiers selected from ethoxylated amines, alkyl ether sulfates, phosphate esters, sorbitan derivatives, alkylphenols, and block copolymers of propylene oxide and ethylene oxide.

5. A composition of claim 1 wherein said triazine herbicide is selected from ametryn, atrazine, cyanazine, desmetryn, dimethametryn, prometon, prometryn, propazine, simazine, simetryn, terbumetron, terbuthylazine, terbutryn and trietazine.

6. A composition of claim 5 wherein said triazine herbicide is atrazine.

7. A composition of claim 6 wherein said chloroacetamide herbicide is acetochlor.

8. A composition of claim 6 wherein said chloroacetamide herbicide is metolachlor.

9. A composition of claim 1 wherein said chloroacetamide herbicide is selected from acctochlor, alachlor, butachlor, dimethachlor, dimethenamid, metazachlor, metolachlor, pretilachlor, propachlor, propisochlor and thenylchlor.

10. A composition of claim 9 wherein the chloroacetamide herbicide is acetochlor.

11. A composition of claim 10 having no substantial amount of solvent for said acetochlor.

12. A composition of claim 10 that further comprises a safener in an amount effective to reduce injury to crop plants caused by said acetochlor.

13. A composition of claim 12 wherein said safener is furilazole.

14. A composition of claim 9 wherein the chloroacetamide herbicide is metolachlor.

15. A composition of claim 14 having no substantial amount of solvent for said metolachlor.

16. A composition of claim 14 that further comprises a safener in an amount effective to reduce injury to crop plants caused by said metolachlor.

17. A composition of claim 16 wherein said safener is selected from benoxacor, fenclorim, flurazole, fluxofenim, furilazole and oxabetrinil.

18. A composition of claim 17 wherein said safener is benoxacor or furilazole, and wherein said metolachlor and said safener are present in a ratio by weight of about 5:1 to about 100:1.

19. A method of controlling weeds in a field, comprising diluting a composition of claim 7 in a suitable volume of water in a spray tank to form a spray composition, and applying said spray composition at a time $T_0$ by means of a sprayer fed from the spray tank to a soil surface in the field and to foliage of weeds that have emerged above the soil surface, whereby (i) said emerged weeds are killed or controlled and (ii) emergence of weeds that would otherwise emerge during a period of about 10 days immediately following To is inhibited.

20. A method of controlling weeds in a field, comprising diluting a composition of claim 1 in a suitable volume of water in a spray tank to form a spray composition, and applying said spray composition at a time $T_0$ by means of a sprayer fed from the spray tank to a soil surface in the field and to foliage of weeds that have emerged above the soil surface, whereby (i) said emerged weeds are killed or controlled and (ii) emergence of weeds that would otherwise emerge during a period of about 10 days immediately following To is inhibited.

21. A method of claim 20 wherein the spray composition is applied to a field in which no crop is planted either shortly before or shortly after application.

22. A method of claim 20 wherein a crop is planted in the field within a period of time from shortly before $T_0$ until about 30 days after To.

23. A method of claim 22 wherein said crop is corn.

24. A method of claim 20 wherein the spray composition is applied to foliage of crop and weed plants and to the soil surface, and wherein said crop has tolerance of herbicidal activity of the foliar-active herbicide.

25. A method of claim 24 wherein said crop has been bred by methods involving genetic transformation.

26. A method of claim 25 wherein said crop is corn.

* * * * *